United States Patent [19]
Fritz et al.

[11] Patent Number: 5,792,763
[45] Date of Patent: Aug. 11, 1998

[54] SEROTONIN 5-HT$_{1F}$ AGONISTS

[75] Inventors: James E. Fritz, McCordsville; Stephen W. Kaldor, Indianapolis; Sidney Xi Liang, Fishers; Upinder Singh, Indianapolis; Yao-Chang Xu, Fishers, all of Ind.

[73] Assignee: Eli Lilly and Company, Indianapolis, Ind.

[21] Appl. No.: 938,739

[22] Filed: Sep. 26, 1997

Related U.S. Application Data

[60] Provisional application No. 60/027,424, Oct. 8, 1996.
[51] Int. Cl.$^6$ .................. A61K 31/54; A61K 31/535; A61K 31/445; C07D 417/00
[52] U.S. Cl. .................. 514/228.2; 514/233.5; 514/253; 514/316; 514/320; 514/324; 514/422; 514/443; 514/470; 544/60; 544/62; 544/129; 544/145; 544/153; 544/360; 544/364; 544/376; 544/187; 544/196; 544/202; 548/525; 549/57; 549/467
[58] Field of Search .................. 514/228.2, 233.5, 514/253, 316, 320, 324, 422, 443, 470; 544/60, 62, 129, 145, 153, 360, 364, 376; 546/187, 196, 202; 548/525; 549/57, 467

[56] References Cited

U.S. PATENT DOCUMENTS 4,847,254  7/1989  Boegesoe et al. .................. 514/256

*Primary Examiner*—William R. A. Jarvis
*Attorney, Agent, or Firm*—Robert D. Titus; David E. Boone

[57] ABSTRACT

This invention provides novel 5-HT$_{1F}$ agonists of formula

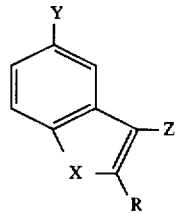

I where X, Y, Z, and R are defined in the specification, which are useful for the prevention and treatment of migraine and associated disorders.

14 Claims, No Drawings

SEROTONIN 5-HT$_{1F}$ AGONISTS

BACKGROUND OF THE INVENTION

This application claims priority to provisional application Ser. No. 60/027,424, filed Oct. 8, 1996.

Theories regarding the pathophysiology of migraine have been dominated since 1938 by the work of Graham and Wolff (*Arch. Neurol. Psychiatry,* 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.,* 600, 587–600 (1990)). Recent work by Moskowitz has shown, however, that the occurrence of migraine headaches is independent of changes in vessel diameter (*Cephalalgia,* 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology,* 43(suppl. 3), S16–S20 (1993)).

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA,* 90, 408–412 (1993)). This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

SUMMARY OF THE INVENTION

The present invention provides the novel benzothiophenes and benzofurans of Formula I:

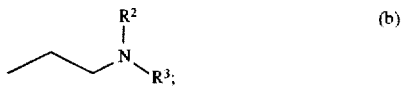

in which

X is O or S;

Y is R$^4$C(O)NH—, R$^5$R$^6$NC(Q)NH—, R$^7$OC(O)NH—, or R$^8$SO$_2$NH—;

Z is a structure of formula:

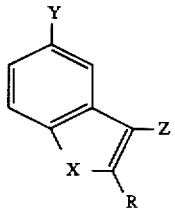

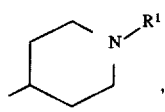

R is hydrogen or C$_1$–C$_4$ alkyl;

R$^1$ is hydrogen or C$_1$–C$_4$ alkyl;

R$^2$ is C$_1$–C$_4$ alkyl, C$_3$–C$_8$ cycloalkyl, cycloalkyl-(C$_1$–C$_3$ alkylene), aryl-(C$_1$–C$_3$ alkylene), or heteroaryl-(C$_1$–C$_3$ alkylene);

R$^3$ is hydrogen or C$_1$–C$_4$ alkyl;

R$^4$ is C$_1$–C$_4$ alkyl, C$_1$–C$_4$ alkoxy substituted C$_1$–C$_4$ alkyl, C$_3$–C$_7$ cycloalkyl, phenyl, substituted phenyl, biphenylyl, naphthyl, or a heterocycle;

R$^5$ and R$^6$ are independently selected from the group consisting of hydrogen, C$_1$–C$_6$ alkyl, C$_3$–C$_6$ alkenyl, C$_3$–C$_8$ cycloalkyl, phenyl, substituted phenyl, phenyl (C$_1$–C$_4$ alkylene), phenyl(C$_1$–C$_4$ alkylene) substituted in the phenyl ring, ((C$_1$–C$_4$ alkyl or C$_1$–C$_4$ alkoxycarbonyl substituted)C$_1$–C$_4$ alkyl)phenyl, C$_1$–C$_4$ alkyl α-substituted with C$_1$–C$_4$ alkoxycarbonyl; or R$^5$ and R$^6$ taken together with the nitrogen atom to which they are attached form a pyrrolidine, piperidine, piperazine, 4-substituted piperazine, morpholine or thiomorpholine ring;

R$^7$ is C$_1$–C$_6$ alkyl, C$_3$–C$_6$ alkenyl, phenyl, substituted phenyl, C$_3$–C$_8$ cycloalkyl, C$_1$–C$_4$ alkyl ω-substituted with C$_1$–C$_4$ alkoxy;

R$^8$ is C$_1$–C$_4$ alkyl, phenyl, substituted phenyl, or di(C$_1$–C$_4$ alkyl)amino;

Q is S or O, and pharmaceutically acceptable acid addition salts thereof.

This invention also provides a pharmaceutical formulation which comprises, in association with a pharmaceutically acceptable carrier, diluent or excipient, a compound of Formula I.

The present invention provides a method for increasing activation of the 5-HT$_{1F}$ receptor by administering to a mammal in need of such activation a pharmaceutically effective amount of a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, allergic rhinitis, cold symptoms, trichotillomania, trigeminal neuralgia, dental pain or temperomandibular joint dysfunction pain. The compounds of this invention are also useful as a prophylactic treatment for migraine. Any of these methods employ a compound of Formula I.

The use of a compound of Formula I for the activation of the 5-HT$_{1F}$ receptor, for the inhibition of peptide extravasation in general or due to stimulation of the trigeminal ganglia specifically, and for the treatment of any of the disorders described supra, are all embodiments of the present invention.

This invention also provides the use of a compound of Formula I for the manufacture of a medicament for the prevention or treatment of migraine and associated disorders. Additionally, this invention provides a pharmaceutical formulation adapted for the prevention or treatment of migraine containing a compound of Formula I. Furthermore, this invention includes a method for the prevention or treatment of migraine which comprises administering an effective amount of a compound of Formula I.

DETAILED DESCRIPTION OF THE INVENTION

The general chemical terms used in the formulae above have their usual meanings. For example, the terms "alkyl, alkoxy and alkylthio" include such groups as methyl, ethyl, n-propyl, isopropyl, n-butyl, isobutyl, sec-butyl, tert-butyl, and the like. The term "cycloalkyl" includes cyclopropyl, cyclobutyl, cyclopentyl, cyclohexyl, and cycloheptyl. The term "acyl" includes formyl, acetyl, propanoyl, butanoyl, and 2-methylpropanoyl. The term "($C_1$–$C_4$ alkyl)sulfonyl" includes methanesulfonyl, ethanesulfonyl, propanesulfonyl, isopropanesulfonyl, butanesulfonyl and the like. The term "halogen" includes fluoro, chloro, bromo and iodo.

The term "substituted phenyl" is taken to mean a phenyl ring substituted with 1 to 3 substitutents independently selected from the group consisting of halogen, $C_1$–$C_4$ alkoxy, $C_1$–$C_4$ alkylthio, $C_1$–$C_4$ alkyl, $C_1$–$C_4$ alkylsulfonyl, nitro, trifluoromethyl, N-($C_1$–$C_4$ acyl)amino, N-($C_1$–$C_4$ alkyl)-N-($C_1$–$C_4$ acyl)amino, N,N-di($C_1$–$C_4$ alkyl)amino and $C_1$–$C_4$ alkoxycarbonyl.

The term "heterocycle" is taken to mean a thienyl, benzothienyl, furyl, benzofuryl, isobenzofuryl, pyrrolyl, 1-($C_1$–$C_3$ alkyl)pyrrolyl, imidazolyl, pyrazolyl, 1-($C_1$–$C_3$ alkyl)pyrazolyl, pyridyl, pyrazinyl, pyrimidinyl, pyridazinyl, indolyl, indazolyl, quinolinyl, isoquinolin-yl, quinoxalinyl, thiazolyl, benzothiazolyl, oxazolyl, benzoxazolyl, 1,3-benzodioxolyl, 1,4-benzodioxanyl, isoxazolyl, benzisoxazolyl, oxadiazolyl or triazolyl bonded through any available ring carbon atom. Each of these rings may be substituted on available ring carbon atoms with up to two substituents independently selected from the group consisting of halo, hydroxy, $C_1$–$C_4$ alkyl, $C_1$–$C_4$ alkoxy, $C_1$–$C_4$ alkylthio, hydroxy substituted ($C_1$–$C_4$ alkylene), cyano, carboxamido, nitro, amino, or di($C_1$–$C_4$ alkyl)amino.

The term "cycloalkyl-($C_1$–$C_3$ alkylene)" is taken to be an alkylene chain of 1–3 carbon atoms which may be monosubstituted with a methyl group and to which is bonded a $C_3$–$C_8$ cycloalkyl moiety.

The term "aryl-($C_1$–$C_3$ alkylene)" is taken to be an alkylene chain of 1–3 carbon atoms which may be monosubstituted with a methyl group and to which is bonded a phenyl or substituted phenyl moiety.

The term "heteroaryl-($C_1$–$C_3$ alkylene)" is taken to be an alkylene chain of 1–3 carbon atoms optionally monosubstituted with a methyl group and to which is bonded a heterocycle.

The term "4-substituted piperazine" is taken to mean a piperazine ring substituted at the 4-position with a substituent selected from the group consisting of $C_1$–$C_6$ alkyl, $C_1$–$C_4$ alkoxy substituted $C_1$–$C_6$ alkyl, phenyl, substituted phenyl, phenyl($C_1$–$C_4$ alkylene), phenyl($C_1$–$C_4$ alkylene) substituted in the phenyl ring, heteroaryl, and heteroaryl ($C_1$–$C_4$ alkylene).

While all of the compounds of this invention are useful as 5-$HT_{1F}$ agonists, certain classes are preferred. The following paragraphs describe such preferred classes.

aa) X is S;
ab) X is O;
ac) R is H;
ad) R is $C_1$–$C_4$ alkyl;
ae) R is methyl;
af) Z is moiety (a);
ag) $R^1$ is H;
ah) $R^1$ is $C_1$–$C_4$ alkyl;
ai) $R^1$ is methyl;
aj) Z is moiety (b);
ak) $R^2$ is $C_1$–$C_4$ alkyl;
al) $R^2$ is methyl;
am) $R^2$ is ethyl;
an) $R^2$ is aryl-($C_1$–$C_3$ alkylene);
ao) $R^2$ is 1-phenyl-1-ethyl;
ap) $R^2$ is 2-phenylethyl;
aq) $R^2$ is heteroaryl-($C_1$–$C_3$ alkylene);
ar) $R^2$ is 2-(1-($C_1$–$C_4$ alkyl)pyrazol-4-yl)ethyl;
as) $R^2$ is (pyridin-2-yl)methyl;
at) $R^2$ is 3-thienylmethyl;
au) $R^2$ is 3-indolylmethyl;
av) $R^2$ is 2-thienylmethyl;
aw) $R^2$ is 2-furylmethyl;
ax) $R^2$ is (5-methylfur-2-yl)methyl;
ay) $R^2$ is (1-methylpyrrol-2-yl)methyl;
az) $R^2$ is (5-hydroxymethylfur-2-yl)methyl;
ba) $R^2$ is (6-chloro-1,3-benzodioxol-5-yl)methyl;
bb) $R^2$ is (3-methylbenzothien-2-yl)methyl;
bc) $R^2$ is cycloalkyl-($C_1$–$C_3$ alkylene);
bd) $R^3$ is hydrogen;
be) $R^3$ is $C_1$–$C_4$ alkyl;
bf) $R^3$ is methyl;
bg) Y is $R^4C(O)NH$—;
bh) Y is $R^5R^6NC(Q)NH$—;
bi) Y is $R^7OC(O)NH$—;
bj) Y is $R^8SO_2NH$—;
bk) $R^4$ is $C_1$–$C_4$ alkyl;
bl) $R^4$ is $C_3$–$C_7$ cycloalkyl;
bm) $R^4$ is substituted phenyl;
bn) $R^4$ is phenyl;
bo) $R^4$ is phenyl monosubstituted with halogen;
bp) $R^4$ is 4-fluorophenyl;
bq) $R^4$ is phenyl disubstituted with halogen;
br) $R^4$ is phenyl 2,6-disubstituted with halogen;
bs) $R^4$ is phenyl 2,4-disubstituted with halogen;
bt) $R^4$ is 2-chloro-4-fluorophenyl;
bu) $R^4$ is phenyl trisubstituted with halogen;
bv) $R^4$ is phenyl 2,4,6-trisubstituted with halogen;
bw) $R^4$ is 2-methyl-4-fluorophenyl;
bx) $R^4$ is a heterocycle;
by) $R^4$ is thienyl;
bz) $R^4$ is furyl;
ca) $R^5$ is H;
cb) $R^6$ is $C_1$–$C_4$ alkyl;
cc) $R^6$ is methyl;
cd) $R^6$ is ethyl;

ce) $R^6$ is propyl;
cf) $R^6$ is isopropyl;
cg) $R^6$ is phenyl;
ch) $R^6$ is $C_3$–$C_8$ alkenyl;
ci) $R^6$ is allyl;
cj) $R^6$ is phenyl monosubstituted with halo;
ck) $R^6$ is 4-fluorophenyl;
cl) $R^6$ is 4-chlorophenyl;
cm) $R^6$ is phenyl($C_1$–$C_4$ alkylene)
cn) $R^6$ is benzyl;
co) $R^6$ is phenethyl;
cp) $R^5$ and $R^6$ taken together with the nitrogen to which they are attached form a morpholine ring;
cq) $R^5$ and $R^6$ taken together with the nitrogen to which they are attached form a thiomorpholine ring;
cr) $R^5$ and $R^6$ taken together with the nitrogen to which they are attached form a pyrrolidine ring;
cs) $R^5$ and $R^6$ taken together with the nitrogen to which they are attached form a piperidine ring;
ct) $R^5$ and $R^6$ taken together with the nitrogen to which they are attached form a pyrrolidine ring;
cu) $R^5$ and $R^6$ taken together with the nitrogen to which they are attached form a piperazine ring;
cv) $R^5$ and $R^6$ taken together with the nitrogen to which they are attached form a 4-substituted piperazine ring;
cw) $R^7$ is $C_1$–$C_4$ alkyl;
cx) $R^7$ is methyl;
cy) $R^7$ is ethyl;
cz) $R^7$ is propyl;
da) $R^7$ is $C_3$–$C_6$ alkenyl;
db) $R^7$ is allyl;
dc) $R^7$ is $C_3$–$C_8$ cycloalkyl;
dd) $R^7$ is cyclopentyl;
de) $R^7$ is phenyl monosubstituted with $C_1$–$C_4$ alkoxy;
df) $R^7$ is 4-methoxyphenyl;
dg) $R^8$ is $C_1$–$C_4$ alkyl;
dh) $R^8$ is methyl;
di) $R^8$ is ethyl;
dj) $R^8$ is phenyl;
dk) $R^8$ is di($C_1$–$C_4$ alkyl)amino;
dl) R8 is dimethylamino;
dm) Q is O;
dn) Q is S;
do) The compound is a free base;
dp) The compound is a salt;
dq) The compound is the hydrochloride salt;
dr) The compound is the fumarate salt;
ds) The compound is the oxalate salt.

It will be understood that the above classes may be combined to form additional preferred classes.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyrophos-phate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

The following group is illustrative of compounds contemplated within the scope of this invention:

N-[2-methyl-3-(2-[N',N'-diethylamino]ethyl)benzofur-5-yl]-4-propanesulfonylbenzamide hydrochloride;

N-[2-ethyl-3-(2-[N'-methyl-N'-isopropylamino]ethyl) benzofur-5-yl]-3-ethylthiobenzamide hydroiodide;

N-[2-propyl-3-(2-[N'-ethyl-N'-cyclopentylpropylamino] ethyl)benzofur-5-yl]-4-ethyl-2-propoxycarbonylbenzamide hydrobromide;

N-[2-isopropyl-3-(2-[N',N'-dibutylamino]ethyl)benzofur-5-yl]-4-(N",N"-dipropylamino)benzamide oxalate;

N-[2-n-butyl-3-(2-[N'-methyl-N'-benzylamino]ethyl)-benzofur-5-yl]-4-isopropylbenzamide sulfate;

N-[2-isobutyl-3-(2-[N'-methyl-N'-cyclopropylmethylamino]ethyl)benzofur-5-yl]-4-(N"-ethyl-N"-butanoyl)aminobenzamide acetate;

N-[2-s-butyl-3-(2-[N'-methyl-N'-(2-[1-propylpyrazol-4-yl]ethyl)amino]ethyl)benzofur-5-yl]-2-nitrobenzamide phosphate;

N-[2-t-butyl-3-(2-[N'-methyl-N'-(1-ethylpyrazol-4-ylmethyl)amino]ethyl)benzofur-5-yl]-4-isobutylsulfonylbenzamide malonate;

N-[2-methyl-3-(2-[N'-methyl-N'-isobutylamino]ethyl) benzofur-5-yl]-3-ethylbenzamide tartrate;

N-[2-methyl-3-(2-[N'-methyl-N'-(2-[pyridin-4-yl]ethyl) amino]ethyl)benzofur-5-yl]-3-t-butoxybenzamide citrate;

N-[2-methyl-3- (2- [N'-methyl-N'-s-butylamino]ethyl) benzofur-5-yl]-4-formylamino-2-propylbenzamide 4-toluenesulfonate;

N-[2-methyl-3-(2-[N'-methyl-N'-(2-[4-bromopyridin-3-yl]-ethyl)amino]ethyl)benzofur-5-yl]-3-t-butoxybenzamide benzoate;

N-[2-methyl-3-(2-[N'-methyl-N'-(2-[1-isopropylpyrazol-4-yl]ethyl)amino]ethyl)benzofur-5-yl]-4-isopropylthiobenzamide fumarate;

N-[2-ethyl-3-(2-[N',N'-diethylamino]ethyl)benzofur-5-yl]-4-fluorobenzamide naphthalene-1-sulfonate;

N-[2-propyl-3-(2-[N'-ethyl-N'-cyclopentylpropyl-amino] ethyl)benzofur-5-yl]-4-bromobenzamide phthalate;

N-[2-isopropyl-3-(2-[N',N'-dibutylamino]ethyl)benzofur-5-yl]-4-fluorobenzamide methanesulfonate;

N-[2-n-butyl-3-(2-[N'-methyl-N'-benzylamino]ethyl) benzofur-5-yl]-4-fluorobenzamide;

N-[2-isobutyl-3-(2-[N'-methyl-N'-cyclopropylmethylamino]ethyl)benzofur-5-yl]-4-iodobenzamide naphthalene-1-sulfonate;

N-[2-s-butyl-3-(2-[N'-methyl-N'-(2-[1-propylpyrazol-4-yl]ethyl)amino]ethyl)benzofur-5-yl]-4-fluorobenzamide ditoluoyltartrate;

N-[2-methyl-3-(2-[N'-methyl-N'-s-butylamino]ethyl) benzofur-5-yl]-isobutyramide;

N-[2-methyl-3-(2-[N'-methyl-N'-(2-[pyridin-4-yl] ethylamino]ethyl)benzofur-5-yl]-4-fluorobenzamide malonate;

N-[2-methyl-3-(2-[N'-methyl-N'-(2-[1-isopropylpyr-azol-4-yl]ethyl)amino]ethyl)benzofur-5-yl]butyramide mandelate;

N-[3-(2-[N'-methyl-N'-([4-bromothien-2-yl]methyl) amino]ethyl)benzofur-5-yl]-4-fluorobenzamide hydrochloride;

N-[2-ethyl-3-(2-[N'-ethyl-N'-(2-[3-methylthiobenzo-fur-5-yl]ethyl)amino]ethyl)benzofur-5-yl]pyridine-2-carboxamide;

N-[2-propyl-3-(2-[N'-isopropyl-N'-(3-[isobenzofur-2-yl] propyl)amino]ethyl)benzofur-5-yl]-4-fluorobenzamide;

N-[2-methyl-3-(2-[N'-butyl-N'-([pyrrol-3-yl]methyl) amino]ethyl)benzofur-5-yl]-4-fluorobenzamide maleate;

N-[2-methyl-3-(2-[N'-methyl-N'-([5-cyanoimidazol-2-yl] methyl)amino]ethyl)benzofur-5-yl]acetamide trifluoroacetate;

N-[2-methyl-3-(2-[N'-methyl-N'-([6-carboxamidopyra-zin-2-yl]methyl)amino]ethyl)benzofur-5-yl] propanamide;

N-[2-methyl-3-(2-[N'-methyl-N'-([5-nitropyrimidin-2-yl] methyl)amino]ethyl)benzofur-5-yl]-2-propanamide;

N-[2-methyl-3-(2-[N'-methyl-N'-([5-dimethylaminopyridazin-3-yl]methyl)amino]ethyl) benzofur-5-yl]butyr-amide benzoate;

N-[2-methyl-3-(2-[N'-methyl-N'-([indazol-5-yl]methyl) amino]ethyl)benzofur-5-yl]pentanamide;

N-[2-methyl-3-(2-[N'-methyl-N'-([quinolin-4-yl]methyl) amino] ethyl)benzofur-5-yl]cyclopropanecarboxamide;

N-[2-methyl-3-(2-[N'-methyl-N'-([isoquinolin-7-yl] methyl)amino]ethyl)benzofur-5-yl] cyclobutanecarboxamide;

N-[2-methyl-3-(2-[N'-methyl-N'-([quinoxalin-2-yl] methyl)amino]ethyl)benzofur-5-yl] cyclopentanecarboxamide hexanoate;

N-[2-methyl-3-(2-[N'-methyl-N'-([quinazolin-5-yl] methyl)amino]ethyl)benzofur-5-yl] cyclohexanecarboxamide;

N-[2-methyl-3-(2-[N'-methyl-N'-([thiazol-2-yl]methyl) amino]ethyl)benzofur-5-yl]cycloheptanecarboxamide;

N-[2-methyl-3-(2-[N'-methyl-N'-([2-aminobenzothia-zol-5-yl]methyl)amino]ethyl)benzofur-5-yl]-4-fluorobenz-amide trifluoromethanesulfonate;

N-[2-methyl-3-(2-[N'-methyl-N'-([oxazol-5-yl]methyl) amino]ethyl)benzofur-5-yl]-3-iodobenzamide;

N-[2-methyl-3-(2-[N'-methyl-N'-([6-nitrobenzoxazol-2-yl]methyl)amino]ethyl)benzofur-5-yl]-2-chlorobenzamide hydrobromide;

N-[2-methyl-3-(2-[N'-methyl-N'-([1.4-benzodioxan-6-yl] methyl)amino]ethyl)benzofur-5-yl]-2-chloropyridine-3-carboxamide;

N-[2-isopropyl-3-(2-[N'-methyl-N'-([isoxazol-4-yl] methyl)amino]ethyl)benzofur-5-yl]benzamide;

N-[2-methyl-3-(2-[N'-methyl-N'-([benzisoxazol-3-yl] methyl)amino]ethyl)benzofur-5-yl]thiophene-2-carboxamide;

N-[2-methyl-3-(2-[N'-methyl-N'-([1,3,4-oxadiazol-2-yl] methyl)amino]ethyl)benzofur-5-yl]furan-3-carboxamide;

N-[2-methyl-3-(2-[N'-methyl-N'-([1,2,3-triazol-4-yl] methyl)amino]ethyl)benzofur-5-yl]-4-fluorobenzamide tosylate;

N-[3-(2-[N'-methyl-N'-((4-bromothien-2-yl)methyl) amino]ethyl)benzofur-5-yl)]-4-fluorobenzamide hydrochloride;

N-[2-ethyl-3-(2-[N'-ethyl-N'-((3-methylthiobenzofur-5-yl)ethyl)amino]ethyl)benzofur-5-yl]pyridine-2-carboxamide;

N-[2-propyl-3-(2-[N'-isopropyl-N'-1-((isobenzofur-2-yl) prop-3-yl)amino]ethyl)benzofur-5-yl]-4-fluorobenzamide;

N-[2-methyl-3-(2-[N'-butyl-N'-(pyrrol-3-yl)methyl) amino]ethyl)benzofur-5-yl]-4-fluorobenzamide maleate;

N-[2-methyl-3-(2-[N'-methyl-N'-((5-cyanoimidazol-2-yl) methyl)amino]ethyl)benzofur-5-yl]-4-acetamide trifluoroacetate;

N-[2-methyl-3-(2-[N'-methyl-N'-((6-carboxamidopyra-zin-2-yl)methyl)amino]ethyl)benzofur-5-yl] propanamide;

N-[2-methyl-3-(2-[N'-methyl-N'-((5-nitropyrimidin-2-yl) methyl)amino]ethyl)benzofur-5-yl]-2-propanamide;

N-[2-methyl-3-(2-[N'-methyl-N'-((5-dimethylaminopyridazin-3-yl)methyl)amino]ethyl) benzofur-5-yl]butyramide benzoate;

N-[2-methyl-3-(2-[N'-methyl-N'-((indazol-5-yl)methyl) amino]ethyl)benzofur-5-yl]pentanamide;

N-[2-methyl-3-(2-[N'-methyl-N'-((quinolin-4-yl)methyl) amino]ethyl)benzofur-5-yl]cyclopropanecarboxamide;

N-[2-methyl-3-(2-[N'-methyl-N'-((isoquinolin-7-yl) methyl)amino]ethyl)benzofur-5-yl] cyclobutanecarboxamide;

N-[2-methyl-3-(2-[N'-methyl-N'-((quinoxalin-2-yl) methyl)amino]ethyl)benzofur-5-yl] cyclopentanecarboxamide acetate;

N-[2-methyl-3-(2-[N'-methyl-N'-((quinazolin-5-yl) methyl)amino]ethyl)benzofur-5-yl] cyclohexanecarboxamide;

N-[2-methyl-3-(2-[N'-methyl-N'-((thiazol-2-yl)methyl) aminoethyl)benzofur-5-yl]cycloheptanecarboxamide;

N-[2-methyl-3-(2-[N'-methyl-N'-((2-aminobenzothia-zol-5-yl)methyl)amino]ethyl)benzofur-5-yl]-4-fluorobenz-amide trifluoromethanesulfonate;

N-[2-methyl-3-(2-[N'-methyl-N'-(2-[pyridin-4-yl]ethyl) amino]ethyl)benzofur-5-yl]-N"-ethylurea;

N-[2-methyl-3-(2-[N'-methyl-N'-s-butylamino]ethyl) benzofur-5-yl]-N"-isopropylurea;

N-[2-methyl-3-(2-[N'-methyl-N'-(2-[pyridin-4-yl]ethyl) amino]ethyl)benzofur-5-yl]-N"-[(3-methoxy)phenyl] urea malonate;

N-[3-(2-[N'-methyl-N'-([4-bromothien-2-yl]methyl) amino]ethyl)benzofur-5-yl]-N"-[(4-isopropoxy) phenyl]urea hydrochloride;

N-[2-propyl-3-(2-[N'-isopropyl-N'-(3-[isobenzofur-2-yl] propyl)amino]ethyl)benzofur-5-yl]-N"-[(2-bromo-3-iodo)phenyl]urea;

N-|2-methyl-3-(2-|N'-butyl-N'-(|pyrrol-3-yl|methyl)amino|ethyl)benzofur-5-yl|-N"-benzylurea maleate;

N-|2-methyl-3-(2-|N'-methyl-N'-(|5-cyanoimidazol-2-yl|methyl)amino|ethyl)benzofur-5-yl|-N"-phenethylurea trifluoroacetate;

N-|2-methyl-3-(2-|N'-methyl-N'-(|6-carboxamidopyrazin-2-yl|methyl)amino|ethyl)benzofur-5-yl|-N"-|4-phenbutyl|urea;

N-|2-methyl-3-(2-|N'-methyl-N'-(|5-nitropyrimidin-2-yl|methyl)amino|ethyl)benzofur-5-yl|-N"-|(2-trifluoromethyl)phenyl|urea;

N-|2-methyl-3-(2-|N'-methyl-N'-(|5-dimethylaminopyridazin-3-yl|methyl)amino|ethyl)benzofur-5-yl|-N"-|(3-phenyl)phenyl|urea benzoate;

1-{|2-methyl-3-(2-[N'-methyl-N'-(|indazol-5-yl]methyl)amino|ethyl)benzofur-5-yl|carbonyl}pyrrolidine;

1-{|2-methyl-3-(2-[N'-methyl-N'-(|quinolin-4-yl]methyl)amino|ethyl)benzofur-5-yl|carbonyl}piperidine;

1-{|2-methyl-3-(2-[N'-methyl-N'-(|isoquinolin-7-yl]methyl)amino|ethyl)benzofur-5-yl] carbonyl}piperazine;

1-{|2-methyl-3-(2-[N'-methyl-N'-(|quinoxalin-2-yl]methyl)amino|ethyl)benzofur-5-yl|carbonyl}-4-methylpiperazine hexanoate;

1-{|2-isopropyl-3-(2-[N'-methyl-N'-(|quinazolin-5-yl]methyl)amino|ethyl)benzofur-5-yl|carbonyl}-4-phenylpiperazine;

1-{|3-(2-[N'-([thiazol-2-yl]methyl)amino]ethyl)benzofur-5-yl|carbonyl}-4-benzylpiperazine;

1-{|2-methyl-3-(2-[N'-([2-aminobenzothiazol-5-yl]methyl)amino]ethyl)benzofur-5-yl|carbonyl}-4-(2,4-dichlorophenyl)piperazine trifluoromethanesulfonate;

1-{|3-(2-[N'-methyl-N'-([oxazol-5-yl]methyl)amino]ethyl)benzofur-5-yl|carbonyl}morpholine;

1-{|2-methyl-3-(2-[N'-methyl-N'-([6-nitrobenzoxazol-2-yl]methyl)amino]ethyl)benzofur-5-yl]carbonyl}thiomorph-oline hydrobromide;

N-[2-methyl-3-(2-[N'-methyl-N'-(2-[pyridin-4-yl]ethyl)amino]ethyl)benzofur-5-yl]-N"-ethylthiourea;

N-[2-methyl-3-(2-[N'-methyl-N'-s-butylamino]ethyl)-benzofur-5-yl]-N"-isopropylthiourea;

N-[2-methyl-3-(2-[N'-methyl-N'-(2-[pyridin-4-yl]ethyl)amino]ethyl)benzofur-5-yl]-N"-[(3-methoxy)phenyl]thiourea malonate;

N-[2-phenyl-3-(2-[N'-methyl-N'-([4-bromothien-2-yl]methyl)amino]ethyl)benzofur-5-yl]-N"-[(4-isopropoxy)phenyl]thiourea hydrochloride;

N-[2-ethyl-3-(2-[N'-ethyl-N'-(2-[3-methylthiobenzo-fur-5-yl]ethyl)amino]ethyl)benzofur-5-yl]-N"-[2,3-dibromophenyl]thiourea;

N-[3-(2-[N'-([pyrrol-3-yl]methyl)amino]ethyl)benzo-fur-5-yl]-N"-benzylthiourea maleate;

N-[3-(2-[N'-methyl-N'-([5-cyanoimidazol-2-yl]methyl)amino|ethyl)benzofur-5-yl]-N"-phenethylthiourea trifluoroacetate;

N-[2-methyl-3-(2-[N'-([6-carboxamidopyrazin-2-yl]methyl)amino]ethyl)benzofur-5-yl]-N"-[4-phenbutyl]thiourea;

N-[2-methyl-3-(2-[N'-methyl-N'-([5-nitropyrimidin-2-yl]methyl)amino]ethyl)benzofur-5-yl]-N"-[(2-trifluoromethyl)phenyl]thiourea;

N-[2-methyl-3-(2-[N'-methyl-N'-([5-dimethylaminopyridazin-3-yl]methyl)amino]ethyl)benzofur-5-yl]-N"-[(3-phenyl)phenyl]thiourea benzoate;

1-{N-[2-methyl-3-(2-[N'-methyl-N'-(|indazol-5-yl|methyl)amino|ethyl)benzofur-5-yl|aminothiocarbonyl}-pyrrolidine;

1-{N-[2-methyl-3-(2-[N'-methyl-N'-(|quinolin-4-yl|methyl)amino|ethyl)benzofur-5-yl|aminothiocarbonyl}-piperidine;

1-{N-[2-methyl-3-(2-[N'-methyl-N'-(|isoquinolin-7-yl|methyl)amino|ethyl)benzofur-5-yl|aminothiocarbonyl}-piperazine;

1-{N-[2-methyl-3-(2-[N'-(|quinoxalin-2-yl]methyl)amino|ethyl)benzofur-5-yl|aminothiocarbonyl}-4-methylpiperazine hexanoate;

1-{N-[2-methyl-3-(2-[N'-methyl-N'-(|quinazolin-5-yl|methyl)amino|ethyl)benzofur-5-yl|aminothiocarbonyl}-4-phenylpiperazine;

1-(N-[2-methyl-3-(2-[N'-methyl-N'-(|thiazol-2-yl|methyl)amino|ethyl)benzofur-5-yl|aminothiocarbonyl}-4-benzylpiperazine;

1-{N-[2-methyl-3-(2-[N'-methyl-N'-(|2-aminobenzothiazol-5-yl|methyl)amino|ethyl)benzofur-5-yl|aminothiocarbonyl}-4-(2,4-dichlorophenyl)piperazine methanesulfonate;

1-{N-[2-methyl-3-(2-[N'-methyl-N'-(|oxazol-5-yl|methyl)amino|ethyl)benzofur-5-yl|aminothiocarbonyl}-morpholine;

1-{N-[2-methyl-3-(2-[N'-methyl-N'-(|6-nitrobenzoxazol-2-yl|methyl)amino|ethyl)benzofur-5-yl|aminothiocarbonyl}thiomorpholine hydrobromide;

N-[2-methyl-3-(2-[N'-(|benzisoxazol-3-yl|methyl)amino]ethyl)benzofur-5-yl|thiophene-2-carboxamide;

N-[2-methyl-3-(2-[N'-(|1,3,4-oxadiazol-2-yl]methyl)amino|ethyl)benzofur-5-yl|furan-3-carboxamide;

N-[2-methyl-3-(2-[N'-(|1,2,3-triazol-4-yl]methyl)amino]ethyl)benzofur-5-yl]-4-fluorobenzamide tosylate;

N-[2-phenyl-3-(2-[N'-((4-bromothien-2-yl)methyl)amino]ethyl)benzofur-5-yl)]-4-fluorobenzamide hydrochloride;

N-[2-ethyl-3-(2-[N'-((3-methylthiobenzofur-5-yl)ethyl)amino]ethyl)benzofur-5-yl]pyridine-2-carboxamide;

N-[2-propyl-3-(2-[N'-1-((isobenzofur-2-yl)prop-3-yl)amino]ethyl)benzofur-5-yl]-4-fluorobenzamide;

N-[2-methyl-3-(2-[N'-(pyrrol-3-yl)methyl)amino]ethyl)benzofur-5-yl]-4-fluorobenzamide maleate;

N-[2-methyl-3-(2-[N'-((5-cyanoimidazol-2-yl)methyl)amino]ethyl)benzofur-5-yl]-4-acetamide trifluoroacetate;

N-[2-methyl-3-(2-[N'-((6-carboxamidopyrazin-2-yl)methyl)amino]ethyl)benzofur-5-yl]propanamide;

5-(N,N-dibutylaminosulfonyl)amino-2-methyl-3-(2-[N'-methyl-N'-((5-nitropyrimidin-2-yl)methyl)amino]ethyl)benzofuran;

5-((N-isopropyl-N-butylamino)sulfonyl)amino-2-methyl-3-(2-[N'-methyl-N'-((5-dimethylaminopyridazin-3-yl)methyl)amino]ethyl)benzofuran benzoate;

5-(dimethylaminosulfonyl)amino-2-methyl-3-(2-[N'-methyl-N'-((indazol-5-yl)methyl)amino]ethyl)benzofuran;

N-[2-methyl-3-(2-[N'-methyl-N'-((quinolin-4-yl)methyl)amino]ethyl)benzofur-5-yl]-4-chlorophenylsulfonamide;

N-[2-methyl-3-(2-[N'-methyl-N'-((isoquinolin-7-yl)methyl)amino]ethyl)benzofur-5-yl]phenylsulfonamide;

N-|2-methyl-3-(2-|N'-methyl-N'-((quinoxalin-2-yl) methyl)amino|ethyl)benzofur-5-yl|butanesulfonamide acetate;

N-|2-methyl-3-(2-|N'-methyl-N'-((quinazolin-5-yl) methyl)amino|ethyl)benzofur-5-yl| isopropanesulfonamide;

5-isopropoxycarbonylamino-2-methyl-3-(2-|N'-methyl-N'-(2-|1-isopropylpyrazol-4-yl|ethyl)amino|ethyl) benzo-furan mandelate;

5-methoxycarbonylamino-(2-[N'-methyl-N'-(|4-bromothien-2-yl|methyl)amino|ethyl)benzofuran hydrochloride;

5-(tert-butoxycarbonyl)amino-2-ethyl-3-(2-[N'-ethyl-N'-(2-|3-methylthiobenzofur-5-yl|ethyl)amino|ethyl) benzofuran;

5-(1-penten-5-yloxy)carbonylamino-2-propyl-3-(2-|N'-isopropyl-N'-(3-|isobenzofur-2-yl|propyl)amino|ethyl) benzofuran;

5-(2-chlorophenoxy)carbonylamino-2-methyl-3-(2-|N'-(|6-carboxamidopyrazin-2-yl|methyl)amino|ethyl) benzo-furan;

5-(3-methoxyphenoxy)carbonylamino-2-methyl-3-(2-|N'-methyl-N'-(|5-dimethylaminopyridazin-3-yl| methyl)amino|ethyl)benzofuran benzoate;

5-cyclopropoxycarbonylamino-2-methyl-3-(2-|N'-methyl-N'-(|indazol-5-yl|methyl)amino|ethyl) benzofuran;

5-cyclooctyloxycarbonylamino-2-methyl-3-(2-|N'-methyl-N'-(|isoquinolin-7-yl|methyl)amino|ethyl) benzo-furan;

5-(butoxymethoxy)carbonylamino-2-methyl-3-(2-[N'-methyl-N'-(|quinoxalin-2-yl|methyl)amino|ethyl) benzofuran hexanoate;

5-(ethoxypropoxy)carbonylamino-N-[2-methyl-3-(2-[N'-methyl-N'-(|quinazolin-5-yl]methyl)amino|ethyl) benzo-furan;

N-[2-methyl-3-(2-[N',N'-diethylamino]ethyl)benzothien-5-yl]-4-propanesulfonylbenzamide hydrochloride;

N-|2-ethyl-3-(2-[N'-methyl-N'-isopropylamino]ethyl) benzothien-5-yl]-3-ethylthiobenzamide hydroiodide;

N-[2-propyl-3-(2-[N'-ethyl-N'-cyclopentylpropylamino] ethyl)benzothien-5-yl]-4-ethyl-2-propoxycarbonylbenzamide hydrobromide;

N-|2-isopropyl-3-(2-[N',N'-dibutylamino]ethyl) benzothien-5-yl]-4-(N'',N''-dipropylamino)benzamide oxalate;

N-|2-n-butyl-3-(2-[N'-methyl-N'-benzylamino]ethyl) benzothien-5-yl]-4-isopropylbenzamide sulfate;

N-[2-isobutyl-3-(2-[N'-methyl-N'-cyclopropylmethylamino]ethyl)benzothien-5-yl]-4-(N''-ethyl-N''-butanoyl)aminobenzamide acetate;

N-[2-s-butyl-3-(2-[N'-methyl-N'-(2-[1-propylpyrazol-4-yl|ethyl)amino]ethyl)benzothien-5-yl]-2-nitrobenzamide phosphate;

N-|2-t-butyl-3-(2-[N'-methyl-N'-(1-ethylpyrazol-4-ylmethyl)amino|ethyl)benzothien-5-yl]-4-isobutylsulfonylbenzamide malonate;

N-|2-methyl-3-(2-[N'-methyl-N'-isobutylamino]ethyl) benzothien-5-yl]-3-ethylbenzamide tartrate;

N-|2-methyl-3-(2-[N'-methyl-N'-(2-[pyridin-4-yl|ethyl) amino|ethyl)benzothien-5-yl]-3-t-butoxybenzamide citrate;

N-|2-methyl-3-(2-[N'-methyl-N'-s-butylamino|ethyl) benzothien-5-yl]-4-formylamino-2-propylbenzamide 4-toluenesulfonate;

N-|2-methyl-3-(2-|N'-methyl-N'-(2-|4-bromopyridin-3-yl|-ethyl)amino|ethyl)benzothien-5-yl|-3-t-butoxybenz-amide benzoate;

N-|2-methyl-3-(2-|N'-methyl-N'-(2-|1-isopropylpyrazol-4-yl|ethyl)amino|ethyl)benzothien-5-yl|-4-isopropylthiobenzamide fumarate;

N-|2-ethyl-3-(2-|N',N'-diethylamino|ethyl)benzothi-en-5-yl|-4-fluorobenzamide naphthalene-1-sulfonate;

N-|2-ethyl-3-(2-|N'-methyl-N'-isopropylamino|ethyl) benzothien-5-yl|-4-fluorobenzamide;

N-|2-isopropyl-3-(2-|N',N'-dibutylamino|ethyl) benzothien-5-yl|-4-fluorobenzamide methanesulfonate;

N-|2-n-butyl-3-(2-|N'-methyl-N'-benzylamino|ethyl)-benzothien-5-yl|-4-fluorobenzamide;

N-|2-isobutyl-3-(2-|N'-methyl-N'-cyclopropylmethylamino|ethyl)benzothien-5-yl|-4-iodobenzamide naphthalene-1-sulfonate;

N-|2-s-butyl-3-(2-|N'-methyl-N'-(2-|1-propylpyrazol-4-yl|ethyl)amino|ethyl)benzothien-5-yl|-4-fluorobenzamide ditoluoyltartrate;

N-|2-t-butyl-3-(2-|N'-methyl-N'-(1-ethylpyrazol-4-ylmethyl)amino|ethyl)benzothien-5-yl|-4-fluorobenzamide;

N-|2-methyl-3-(2-|N'-methyl-N'-isobutylamino|ethyl) benzothien-5-yl|-2-bromo-4-fluorobenzamide;

N-|2-methyl-3-(2-[N'-methyl-N'-(2-[pyridin-4-yl]ethyl) amino]ethyl)benzothien-5-yl]-4-fluorobenzamide;

N-|2-methyl-3-(2-[N'-methyl-N'-s-butylamino]ethyl) benzothien-5-yl|isobutyramide;

N-|2-methyl-3-(2-[N'-methyl-N'-(2-[pyridin-4-yl]ethyl) amino]ethyl)benzothien-5-yl]-4-fluorobenzamide malonate;

N-|2-methyl-3-(2-[N'-methyl-N'-(2-[1-isopropylpyrazol-4-yl]ethyl)amino]ethyl)benzothien-5-yl| butyramide mandelate;

N-|3-(2-[N'-methyl-N'-(|4-bromothien-2-yl|methyl) amino]ethyl)benzothien-5-yl]-4-fluorobenzamide hydrochloride;

N-[2-ethyl-3-(2-[N'-ethyl-N'-(2-[3-methylthiobenzothien-5-yl]ethyl)amino]ethyl)benzothien-5-yl]pyridine-2-carboxamide;

N-|2-propyl-3-(2-[N'-isopropyl-N'-(3-[isobenzofur-2-yl] propyl)amino]ethyl)benzothien-5-yl|-4-fluorobenzamide;

N-|2-methyl-3-(2-[N'-butyl-N'-(|pyrrol-3-yl]methyl) amino]ethyl)benzothien-5-yl]-4-fluorobenzamide maleate;

N-|2-methyl-3-(2-[N'-methyl-N'-(|5-cyanoimidazol-2-yl] methyl)amino]ethyl)benzothien-5-yl|acetamide trifluoroacetate;

N-|2-methyl-3-(2-[N'-methyl-N'-(|6-carboxamidopyrazin-2-yl]methyl)amino]ethyl)benzothien-5-yl| propanamide;

N-|2-methyl-3-(2-[N'-methyl-N'-(|5-nitropyrimidin-2-yl] methyl)amino]ethyl)benzothien-5-yl]-2-propanamide;

N-[2-methyl-3-(2-|N'-methyl-N'-(|5-dimethylaminopyridazin-3-yl]methyl)amino|ethyl) benzothien-5-yl|butyramide benzoate;

N-|2-methyl-3-(2-[N'-methyl-N'-(|indazol-5-yl]methyl) amino]ethyl)benzothien-5-yl]pentanamide;

N-|2-methyl-3-(2-[N'-methyl-N'-(|quinolin-4-yl]methyl) amino]ethyl)benzothien-5-yl| cyclopropanecarboxamide;

N-[2-methyl-3-(2-[N'-methyl-N'-([isoquinolin-7-yl]
    methyl)amino]ethyl)benzothien-5-yl]
    cyclobutanecarbox-amide;
N-[2-methyl-3-(2-[N'-methyl-N'-([quinoxalin-2-yl]
    methyl)amino]ethyl)benzothien-5-yl]
    cyclopentanecarbox-amide hexanoate;
N-[2-methyl-3-(2-[N'-methyl-N'-([quinazolin-5-yl]
    methyl)amino]ethyl)benzothien-5-yl]
    cyclohexanecarbox-amide;
N-[2-methyl-3-(2-[N'-methyl-N'-([thiazol-2-yl]methyl)
    amino]ethyl)benzothien-5-yl]
    cycloheptanecarboxamide;
N-[2-methyl-3-(2-[N'-methyl-N'-([2-aminobenzothia-
    zol-5-yl]methyl)amino]ethyl)benzothien-5-yl]-4-
    fluoro-benzamide trifluoromethanesulfonate;
N-[2-methyl-3-(2-[N'-methyl-N'-([oxazol-5-yl]methyl)
    amino]ethyl)benzothien-5-yl]-3-iodobenzamide;
N-[2-methyl-3-(2-[N'-methyl-N'-([6-nitrobenzoxazol-2-
    yl]methyl)amino]ethyl)benzothien-5-yl]-2-chlorobenz-
    amide hydrobromide;
N-[2-methyl-3-(2-[N'-methyl-N'-([1,4-benzodioxan-6-yl]
    methyl)amino]ethyl)benzothien-5-yl]-2-
    chloropyridine-3-carboxamide;
N-[2-isopropyl-3-(2-[N'-methyl-N'-([isoxazol-4-yl]
    methyl)amino]ethyl)benzothien-5-yl]benzamide;
N-[2-methyl-3-(2-[N'-methyl-N'-([benzisoxazol-3-yl]
    methyl)amino]ethyl)benzothien-5-yl]thiophene-2-
    carbox-amide;
N-[2-methyl-3-(2-[N'-methyl-N'-([1,3,4-oxadiazol-2-yl]
    methyl)amino]ethyl)benzothien-5-yl]furan-3-carbox-
    amide;
N-[2-methyl-3-(2-[N'-methyl-N'-([1,2,3-triazol-4-yl]
    methyl)amino]ethyl)benzothien-5-yl]-4-
    fluorobenzamide tosylate;
N-[3-(2-[N'-methyl-N'-(($^4$-bromothien-2-yl)methyl)
    amino]ethyl)benzothien-5-yl)]-4-fluorobenzamide
    hydrochloride;
N-[$^2$-ethyl-3-(2-[N'-ethyl-N'-((3-methylthiobenzo-thien-
    5-yl)ethyl)amino]ethyl)benzothien-5-yl]pyridine-2-
    carboxamide;
N-[2-propyl-3-(2-[N'-isopropyl-N'-1-((isobenzofur-2-yl)
    prop-3-yl)amino]ethyl)benzothien-5-yl]-4-
    fluorobenzamide;
N-[2-methyl-3-(2-[N'-butyl-N'-(pyrrol-3-yl)methyl)
    amino]ethyl)benzothien-5-yl]-4-fluorobenzamide
    maleate;
N-[2-methyl-3-(2-[N'-methyl-N'-((5-cyanoimidazol-2-yl)
    methyl)amino]ethyl)benzothien-5-yl]-4-acetamide trif-
    luoroacetate;
N-[2-methyl-3-(2-[N'-methyl-N'-((6-carboxamidopyra-
    zin-2-yl)methyl)amino]ethyl)benzothien-5-yl]
    propanamide;
N-[2-methyl-3-(2-[N'-methyl-N'-((5-nitropyrimidin-2-yl)
    methyl)amino]ethyl)benzothien-5-yl]-2-propanamide;
N-[2-methyl-3-(2-[N'-methyl-N'-((5-
    dimethylaminopyridazin-3-yl]methyl)amino]ethyl)
    benzothien-5-yl]butyramide benzoate;
N-[2-methyl-3-(2-[N'-methyl-N'-((indazol-5-yl)methyl)
    amino]ethyl)benzothien-5-yl]pentanamide;
N-[2-methyl-3-(2-[N'-methyl-N'-((quinolin-4-yl)methyl)
    amino]ethyl)benzothien-5-yl]
    cyclopropanecarboxamide;
N-[2-methyl-3-(2-[N'-methyl-N'-((isoquinolin-7-yl)
    methyl)amino]ethyl)benzothien-5-yl]
    cyclobutanecarbox-amide;

N-[2-methyl-3-(2-[N'-methyl-N'-((quinoxalin-2-yl)
    methyl)amino]ethyl)benzothien-5-yl]
    cyclopentanecarbox-amide acetate;
N-[2-methyl-3-(2-[N'-methyl-N'-((quinazolin-5-yl)
    methyl)amino]ethyl)benzothien-5-yl]
    cyclohexanecarbox-amide;
N-[2-methyl-3-(2-[N'-methyl-N'-((thiazol-2-yl)methyl)
    amino]ethyl)benzothien-5-yl]
    cycloheptanecarboxamide;
N-[2-methyl-3-(2-[N'-methyl-N'-((2-aminobenzothia-
    zol-5-yl)methyl)amino]ethyl)benzothien-5-yl]-4-
    fluoro-benzamide trifluoromethanesulfonate;
N-[2-methyl-3-(2-[N'-methyl-N'-(2-[pyridin-4-yl]ethyl)
    amino]ethyl)benzothien-5-yl]-N''-ethylurea;
N-[2-methyl-3-(2-[N'-methyl-N'-s-butylamino]ethyl)
    benzothien-5-yl]-N''-isopropylurea;
N-[2-methyl-3-(2-[N'-methyl-N'-(2-[pyridin-4-yl]ethyl)
    amino]ethyl)benzothien-5-yl]-N''-[(3-methoxy)
    phenyl]-urea malonate;
N-[3-(2-[N'-(2-[1-isopropylpyrazol-4-yl]ethyl)amino]
    ethyl)benzothien-5-yl]-N''-[(2-ethoxy)phenyl]urea
    mandelate;
N-[3-(2-[N'-methyl-N'-([4-bromothien-2-yl]methyl)
    amino]ethyl)benzothien-5-yl]-N''-[(4-isopropoxy)
    phenyl]urea hydrochloride;
N-[2-ethyl-3-(2-[N'-(2-[3-methylthiobenzothien-5-yl]
    ethyl)amino]ethyl)benzothien-5-yl]-N''-[2,3-
    dibromophenyl]urea;
N-[2-propyl-3-(2-[N'-isopropyl-N'-(3-[isobenzofur-2-yl]
    propyl)amino]ethyl)benzothien-5-yl]-N''-[(2-bromo-3-
    iodo)phenyl]urea;
N-[2-methyl-3-(2-[N'-butyl-N'-([pyrrol-3-yl]methyl)
    amino]ethyl)benzothien-5-yl]-N''-benzylurea maleate;
N-[2-methyl-3-(2-[N'-methyl-N'-([5-cyanoimidazol-2-yl]
    methyl)amino]ethyl)benzothien-5-yl]-N''-
    phenethylurea trifluoroacetate;
N-[2-methyl-3-(2-[N'-methyl-N'-([6-carboxamidopyra-
    zin-2-yl]methyl)amino]ethyl)benzothien-5-yl]-N''-[4-
    phen-butyl]urea;
N-[2-methyl-3-(2-[N'-methyl-N'-([5-nitropyrimidin-2-yl]
    methyl)amino]ethyl)benzothien-5-yl]-N''-[(2-
    trifluoromethyl)phenyl]urea;
N-[2-methyl-3-(2-[N'-methyl-N'-([5-
    dimethylaminopyridazin-3-yl]methyl)amino]ethyl)
    benzothien-5-yl]-N''-[(3-phenyl)phenyl]urea benzoate;
1-{[2-methyl-3-(2-[N'-methyl-N'-([indazol-5-yl]methyl)
    amino]ethyl)benzothien-5-yl]carbonyl}pyrrolidine;
1-{[2-methyl-3-(2-[N'-methyl-N'-([quinolin-4-yl]methyl)
    amino]ethyl)benzothien-5-yl]carbonyl}piperidine;
1-{[2-methyl-3-(2-[N'-methyl-N'-([isoquinolin-7-yl]
    methyl)amino]ethyl)benzothien-5-yl]
    carbonyl}piperazine;
1-{[2-methyl-3-(2-[N'-methyl-N'-([quinoxalin-2-yl]
    methyl)amino]ethyl)benzothien-5-yl]carbonyl}-4-
    methylpiperazine hexanoate;
1-{[2-isopropyl-3-(2-[N'-methyl-N'-([quinazolin-5-yl]
    methyl)amino]ethyl)benzothien-5-yl]carbonyl}-4-
    phenylpiperazine;
1-{[3-(2-[N'-([thiazol-2-yl]methyl)amino]
    ethylbenzothien-5-yl]carbonyl}-4-benzylpiperazine;
1-{[2-methyl-3-(2-[N'-([2-aminobenzothiazol-5-yl]
    methyl)amino]ethyl)benzothien-5-yl]carbonyl}-4-(2,4-
    dichlorophenyl)piperazine trifluoromethanesulfonate;

1-{[3-(2-[N'-methyl-N'-([oxazol-5-yl]methyl)amino] ethyl)benzothien-5-yl]carbonyl}morpholine;

1-{[2-methyl-3-(2-[N'-methyl-N'-([6-nitrobenzoxazol-2-yl]methyl)amino]ethyl)benzothien-5-yl]carbonyl} thiomorpholine hydrobromide;

N-[2-methyl-3-(2-[N'-methyl-N'-(2-[pyridin-4-yl]ethyl) amino]ethyl)benzothien-5-yl]-N"-ethylthiourea;

N-[2-methyl-3-(2-[N'-methyl-N'-s-butylamino]ethyl) benzothien-5-yl]-N"-isopropylthiourea;

N-[2-methyl-3-(2-[N'-methyl-N'-(2-[pyridin-4-yl]ethyl) amino]ethyl)benzothien-5-yl]-N"-[(3-methoxy) phenyl]thiourea malonate;

N- [2-methyl-3- (2- [N'-methyl-N'- (2- [1-isopropylpyrazol-4-yl]ethyl)amino]ethyl)benzothien-5-yl]-N"-[(2-ethoxy)phenyl]thiourea mandelate;

N-[2-phenyl-3-(2-[N'-methyl-N'-([4-bromothien-2-yl] methyl)amino]ethyl)benzothien-5-yl]-N"-[(4-isopropoxy)phenyl]thiourea hydrochloride;

N-[2-ethyl-3-(2-[N'-ethyl-N'-(2-[3-methylthiobenzothien-5-yl]ethyl)amino]ethyl) benzothien-5-yl]-N"-[2,3-dibromophenyl]thiourea;

N-[2-propyl-3-(2-[N'-isopropyl-N'-(3-[isobenzofur-2-yl] propyl)amino]ethyl)benzothien-5-yl]-N"-[(2-bromo-3-iodo)phenyl]thiourea;

N-[3-(2-[N'-([pyrrol-3-yl]methyl)amino]ethyl) benzothien-5-yl]-N"-benzylthiourea maleate;

N-[3-(2-[N'-methyl-N'-([5-cyanoimidazol-2-yl]methyl) amino]ethyl)benzothien-5-yl]-N"-phenethylthiourea trifluoroacetate;

N-[2-methyl-3-(2-[N'-([6-carboxamidopyrazin-2-yl] methyl)amino]ethyl)benzothien-5-yl]-N"-[4-phenbutyl]thiourea;

N-[2-methyl-3-(2-[N'-methyl-N'-([5-nitropyrimidin-2-yl] methyl)amino]ethyl)benzothien-5-yl]-N"-[(2-trifluoromethyl)phenyl]thiourea;

N-[2-methyl-3-(2-[N'-methyl-N'-([5-dimethylaminopyridazin-3-yl]methyl)amino]ethyl) benzothien-5-yl]-N"-[(3-phenyl)phenyl]thiourea benzoate;

N- 1-{N-[2-methyl-3-(2-[N'-methyl-N'-([indazol-5-yl] methyl)amino]ethyl)benzothien-5-yl] aminothiocarbonyl}pyrrolidine;

1-{N-[2-methyl-3-(2-[N'-methyl-N'-([quinolin-4-yl] methyl)amino]ethyl)benzothien-5-yl] aminothiocarbonyl}piperidine;

1-{N-[2-methyl-3-(2-[N'-methyl-N'-([isoquinolin-7-yl] methyl)amino]ethyl)benzothien-5-yl] aminothiocarbonyl}piperazine;

1-{N-[2-methyl-3-(2-[N'-([quinoxalin-2-yl]methyl) amino]ethyl)benzothien-5-yl]aminothiocarbonyl}-4-methylpiperazine hexanoate;

1-{N-[2-methyl-3-(2-[N'-methyl-N'-([quinazolin-5-yl] methyl)amino]ethyl)benzothien-5-yl] aminothiocarbonyl}-4-phenylpiperazine;

1-{N-[2-methyl-3-(2-[N'-methyl-N'-([thiazol-2-yl] methyl)amino]ethyl)benzothien-5-yl] aminothiocarbonyl}-4-benzylpiperazine;

1-{N-[2-methyl-3-(2-[N'-methyl-N'-([2-aminobenzothiazol-5-yl]methyl)amino]ethyl) benzothien-5-yl]aminothiocarbonyl}-4-(2,4-dichlorophenyl)piperazine trifluoromethanesulfonate;

1-{N-[2-methyl-3-(2-[N'-methyl-N'-([oxazol-5-yl] methyl)amino]ethyl)benzothien-5-yl] aminothiocarbonyl}morpholine;

1-{N-[2-methyl-3-(2-[N'-methyl-N'-([6-nitrobenzoxazol-2-yl]methyl)amino]ethyl)benzothien-5-yl] aminothiocarbonyl}thiomorpholine hydrobromide;

N-[2-methyl-3-(2-[N'-([benzisoxazol-3-yl]methyl)amino] ethyl)benzothien-5-yl]thiophene-2-carboxamide;

N-[2-methyl-3-(2-[N'-([1,3,4-oxadiazol-2-yl]methyl) amino]ethyl)benzothien-5-yl]furan-3-carboxamide;

N-[2-methyl-3-(2-[N'-([1,2,3-triazol-4-yl]methyl)amino] ethyl)benzothien-5-yl]-4-fluorobenzamide tosylate;

N-[2-phenyl-3-(2-[N'-((4-bromothien-2-yl)methyl) amino]ethyl)benzothien-5-yl)1-4-fluorobenzamide hydrochloride;

N-[2-ethyl-3-(2-[N'-((3-methylthiobenzothien-5-yl)ethyl) amino]ethyl)benzothien-5-yl]pyridine-2-carboxamide;

N-[2-propyl-3-(2-[N'-1-((isobenzofur-2-yl)prop-3-yl) amino]ethyl)benzothien-5-yl]-4-fluorobenzamide;

N-[2-methyl-3-(2-[N'-(pyrrol-3-yl)methyl)amino]ethyl) benzothien-5-yl]-4-fluorobenzamide maleate;

N-[2-methyl-3-(2-[N'-((5-cyanoimidazol-2-yl)methyl) amino]ethyl)benzothien-5-yl]-4-acetamide acetate;

N-[2-methyl-3-(2-[N'-((6-carboxamidopyrazin-2-yl) methyl)amino]ethyl)benzothien-5-yl]propanamide;

5-(N,N-dibutylaminosulfonyl)amino-2-methyl-3-(2-[N'-methyl-N'-((5-nitropyrimidin-2-yl)methyl)amino] ethyl)benzothiophene;

5-((N-isopropyl-N-butylamino)sulfonyl)amino-2-methyl-3-(2-[N'-methyl-N'-((5-dimethylaminopyridazin-3-yl)methyl)amino]ethyl)benzothiophene benzoate;

N-[2-methyl-3-(2-[N'-methyl-N'-((quinolin-4-yl)methyl) amino]ethyl)benzothien-5-yl]-4-chlorophenylsulfonamide;

N-[2-methyl-3-(2-[N'-methyl-N'-((isoquinolin-7-yl) methyl)amino]ethyl)benzothien-5-yl] phenylsulfonamide;

N-[2-methyl-3-(2-[N'-methyl-N'-((quinazolin-5-yl) methyl)amino]ethyl)benzothien-5-yl] isopropanesulfonamide;

N-[2-methyl-3-(2-[N'-((2-aminobenzothiazol-5-yl) methyl)amino]ethyl)benzothien-5-yl] ethanesulfonamide trifluoromethanesulfonate;

5-methoxycarbonylamino-(2-[N'-methyl-N'-([4-bromothien-2-yl]methyl)amino]ethyl)benzothiophene hydrochloride;

5-(tert-butoxycarbonyl)amino-2-ethyl-3-(2-[N'-ethyl-N'-(2-[3-methylthiobenzofur-5-yl]ethyl)amino]ethyl) benzothiophene;

5-(4-hexen-6-yloxy)carbonylamino-3-(2-[N'-methyl-N'-([5-cyanoimidazol-2-yl]methyl)amino]ethyl) benzothiophene trifluoroacetate;

5-(3-bromophenoxy)carbonylamino-3-(2-[N'-([5-nitropyrimidin-2-yl]methyl)amino]ethyl) benzothiophene;

5-(3-methoxyphenoxy)carbonylamino-2-methyl-3-(2-[N'-methyl-N'-([5-dimethylaminopyridazin-3-yl] methyl)amino]ethyl)benzothiophene benzoate;

5-cyclopropoxycarbonylamino-2-methyl-3-(2-[N'-methyl-N'-([indazol-5-yl]methyl)amino]ethyl) benzothio-phene;

5-(butoxymethoxy)carbonylamino-2-methyl-3-(2-[N'-methyl-N'-([quinoxalin-2-yl]methyl)amino]ethyl) benzothiophene hexanoate;

5-(N-butanesulfonyl)amino-3-(piperidin-4-yl) benzofuran;

5-(N-isobutanesulfonyl)amino-3-(1-(sec-butyl)piperidin-4-yl)benzofuran;

5-(N-isopropyl-N-sec-butanesulfonyl)amino-3-(1-(tert-butyl)piperidin-4-yl)benzofuran;

5-(N-(tert-butyl)sulfonyl)amino-3-(1-butylpiperidin-4-yl)benzofuran;

5-(N,N-diethylaminosulfonyl)amino-3-(1-isobutylpiperidin-4-yl)benzofuran;

5-(N,N-dipropylaminosulfonyl)amino-3-(1-ethylpiperidin-4-yl)-2-methylbenzofuran;

5-(N,N-diisopropylaminosulfonyl)amino-3-(1-(2-pentyl)piperidin-4-yl)benzofuran;

5-(N,N-dibutylaminosulfonyl)amino-3-(1-hexylpiperidin-4-yl)benzofuran;

N-propyl-N'-(3-(1-(2-pentyl)piperidin-4-yl)benzofur-5-yl)thiourea;

N-butyl-N'-(3-(1-isopropylpiperidin-4-yl)benzofur-5-yl)thiourea;

N-(2-methoxy)phenyl-N'-(3-(1-(sec-butyl)piperidin-4-yl)benzofur-5-yl)thiourea;

N-(2,3-dibromo)phenyl-N'-(3-(1-isopropylpiperidin-4-yl)benzofur-5-yl)thiourea;

N-(2-chloro-5-iodo)phenyl-N'-(3-(1-hexylpiperidin-4-yl)benzofur-5-yl)thiourea;

N-(3-phenpropyl)-N'-(3-(1-(sec-butyl)piperidin-4-yl)benzofur-5-yl)thiourea;

N-(4-trifluoromethyl)phenyl-N'-(3-(1-neopentylpiperidin-4-yl)benzofur-5-yl)thiourea;

N-(4-phenyl)phenyl-N'-(3-(1-pentylpiperidin-4-yl)benzofur-5-yl)thiourea;

N-hexyl-N'-(3-(1-propylpiperidin-4-yl)benzofur-5-yl)urea;

N-(2-buten-4-yl)-N'-(3-(1-butylpiperidin-4-yl)benzofur-5-yl)urea;

N-(2-penten-5-yl)-N'-(3-(1-(sec-butyl)piperidin-4-yl)benzofur-5-yl)urea;

N-cyclopropyl-N'-(3-(1-hexylpiperidin-4-yl)benzofur-5-yl)urea;

N-(3-iodo)phenyl-N'-(2-methyl-3-(1-butylpiperidin-4-yl)benzofur-5-yl)urea;

N-(3-phenyl)phenyl-N'-(3-(1-propylpiperidin-4-yl)benzofur-5-yl)urea;

N-(4-ethoxy)phenyl-N'-(3-(1-(sec-butyl)piperidin-4-yl)benzofur-5-yl)urea;

N-(4-isopropoxy)phenyl-N'-(3-(1-isobutylpiperidin-4-yl)benzofur-5-yl)urea;

N-(2-formyl)phenyl-N'-(3-(1-(3-pentyl)piperidin-4-yl)benzofur-5-yl)urea;

N-(3-acetyl)phenyl-N'-(3-(1-(2-pentyl)piperidin-4-yl)benzofur-5-yl)urea phenylpropionate;

N-(3-propanoyl)phenyl-N'-(3-(1-pentylpiperidin-4-yl)benzofur-5-yl)urea;

N-(3-propylthio)phenyl-N',-(3-piperidin-4-yl)benzofur-5-yl)urea;

N-(3-isopropylthio)phenyl-N'-(3-(1-isopropylpiperidin-4-yl)benzofur-5-yl)urea;

N-(3-ethyl)phenyl-N'-(3-(1-pentylpiperidin-4-yl)benzofur-5-yl)urea;

N-(3-isopropyl)phenyl-N'-(3-(1-isopropylpiperidin-4-yl)benzofur-5-yl)urea;

N-(3-methoxycarbonyl)phenyl-N'-(3-(1-pentylpiperidin-4-yl)benzofur-5-yl)urea;

N-(2-butoxycarbonyl)phenyl-N'-(3-(1-propylpiperidin-4-yl)benzofur-5-yl)urea;

N-(2,3-dibromo)phenyl-N'-(3-(1-isopropylpiperidin-4-yl)benzofur-5-yl)urea;

N-(3,4-difluoro)phenyl-N'-(3-(1-butylpiperidin-4-yl)benzofur-5-yl)urea;

N-(3-fluoro-5-chloro)phenyl-N'-(3-(1-(2-pentyl)piperidin-4-yl)benzofur-5-yl)urea;

N-(3-phenpropyl)-N'-(3-(1-propylpiperidin-4-yl)benzofur-5-yl)urea;

N-ethyl-N-phenyl-N'-(3-(1-butylpiperidin-4-yl)benzofur-5-yl)urea;

N-propyl-N-isopropyl-N'-(3-(1-isobutylpiperidin-4-yl)benzofur-5-yl)urea;

N,N-diisopropyl-N'-(3-(1-butylpiperidin-4-yl)benzofur-5-yl)urea;

N,N-dibutyl-N'-(3-(1-butylpiperidin-4-yl)benzofur-5-yl)urea;

5-butoxycarbonylamino-3-(1-propylpiperidin-4-yl)-2-propylbenzofuran;

5-(3-hexen-6-yloxy)carbonylamino-3-(1-(3-pentyl)piperidin-4-yl)benzofuran;

5-(3-chlorophenoxy)carbonylamino-3-(1-hexylpiperidin-4-yl)benzofuran;

5-(2-propoxyphenoxy)carbonylamino-3-(1-(2-pentyl)piperidin-4-yl)benzofuran;

5-(4-methoxybutoxy)carbonylamino(1-ethylpiperidin-4-yl)benzofuran;

5-(2-furoyl)amino-3-(1-(tert-butyl)piperidin-4-yl)benzofuran;

5-(propanoyl)amino-3-(1-neopentylpiperidin-4-yl)benzofuran mandalate;

5-(2-methylpropanoyl)amino-3-(1-(3-pentyl)piperidin-4-yl)benzofuran;

5-(2-methyl-4-butyn-1-oyl)amino-3-(1-(tert-butyl)piperidin-4-yl)benzofuran;

5-(2-methylbutanoyl)-N-methylamino-3-(1-ethylpiperidin-4-yl)benzofuran;

5-(hex-3-enoyl)amino-3-(1-propylpiperidin-4-yl)benzofuran;

5-(cyclohexaneacetyl)amino-3-(1-isopropylpiper-idin-4-yl)benzofuran;

5-(cycloheptylcarbonyl)amino-3-(1-butylpiperidin-4-yl)benzofuran;

5-(5-phenylpentanoyl)amino-3-(1-(2-pentyl)piperidin-4-yl)benzofuran;

5-(3-phenoxypropanoyl)amino-3-(1-neopentylpiperidin-4-yl)benzofuran;

5-(5-phenoxypentanoyl)amino-3-(1-neopentylpiperidin-4-yl)benzofuran;

5-(5-methoxypentanoyl)amino-3-(1-isopropylpiperidin-4-yl)benzofuran;

5-(benzoyl-N-ethyl)amino-3-(1-ethylpiperidin-4-yl)benzofuran;

5-benzoylamino-3-(1-hexylpiperidin-4-yl)benzofuran;

5-(2-bromobenzoyl)amino-3-(1-butylpiperidin-4-yl)benzofuran;

5-(4-ethylbenzoyl)amino-3-(1-ethylpiperidin-4-yl)benzofuran;

5-(2-butylbenzoyl)amino-3-(1-butylpiperidin-4-yl)benzofuran;

5-(3-ethoxybenzoyl)amino-3-(1-pentylpiperidin-4-yl) benzofuran;

5-(4-pentyloxybenzoyl)amino-3-(1-methylpiperidin-4-yl) benzofuran;

5-(2-hexyloxybenzoyl)amino-3-(1-pentylpiperidin-4-yl) benzofuran;

5-(3-propylthiobenzoyl)amino-3-(1-propylpiperidin-4-yl) benzofuran;

5-(3-nitrobenzoyl)amino-3-(1-isobutylpiperidin-4-yl) benzofuran;

5-(3-cyanobenzoyl)amino-3-(1-(2-pentyl)piperidin-4-yl) benzofuran;

5-(4-(diethylamino)benzoyl)amino-$^3$-(1-pentylpiperidin-4-yl)benzofuran;

5-(4-trifluoromethoxybenzoyl)amino-$^3$-(1-isopropylpiperidin-4-yl)benzofuran;

5-(2-(formyl)benzoyl)amino-3-(1-neopentylpiperi-din-4-yl)benzofuran;

5-(3-(butanoyl)benzoyl)amino-3-(1-methylpiperidin-4-yl)benzofuran;

5-(2-(benzoyl)benzoyl)amino-3-(1-pentylpiperidin-4-yl)benzofuran;

5-(2-(methanesulfonyl)benzoyl)amino-3-(1-butylpiperidin-4-yl)benzofuran;

5-(2-butanesulfonylbenzoyl)amino-3-(1-isopropylpiperidin-4-yl)benzofuran;

5-(3-phenylbenzoyl)amino-3-(1-(tert-butyl)piperidin-4-yl)benzofuran;

5-(2,3-dibromo)benzoyl-N-isopropylamino-3-(1-isopropylpiperidin-4-yl)benzofuran;

5-(3-fluoro-5-chloro)benzoylamino-3-(1-(2-pentyl) piperidin-4-yl)benzofuran;

5-(2-thienoyl)amino-3-(1-(tert-butyl)piperidin-4-yl) benzofuran;

5-(3-thienoyl)amino-3-(1-pentylpiperidin-4-yl) benzofuran;

5-(2-furoyl)amino-3-(1-hexylpiperidin-4-yl)benzofuran;

5-(3-furoyl)amino-3-(1-isobutylpiperidin-4-yl) benzofuran;

N-[imidazol-4-yl]-5-carboxamido-3-(1-methylpiperidin-4-yl)benzofuran;

N-[pyrimidin-5-yl]-5-carboxamido-3-(1-methylpiperidin-4-yl)benzofuran;

N-[indol-2-yl]-5-carboxamido-3-(1-methylpiperidin-4-yl)benzofuran;

N-[isoxazol-5-yl]-5-carboxamido-3-(1-methylpiperidin-4-yl)benzofuran;

5-(N-isobutanesulfonyl)amino-3-(1-(sec-butyl)piperidin-4-yl)benzothiophene;

5-(N-isopropyl-N-sec-butanesulfonyl)amino-3-(1-(tert-butyl)piperidin-4-yl)benzothiophene;

5-(N-(tert-butyl)sulfonyl)amino-3-(1-butylpiperidin-4-yl) benzothiophene;

5-(N,N-diethylaminosulfonyl)amino-3-(1-isobutylpiperidin-4-yl)benzothiophene;

5-(N,N-diisopropylaminosulfonyl)amino-3-(1-(2-pentyl)-piperidin-4-yl)benzothiophene;

5-(N,N-dibutylaminosulfonyl)amino-3-(1-hexylpiperidin-4-yl)benzothiophene;

N-propyl-N'-(3-(1-(2-pentyl)piperidin-4-yl)benzothien-5-yl)thiourea;

N-butyl-N'-(3-(1-isopropylpiperidin-4-yl)benzothien-5-yl)thiourea;

N-(2-isopropoxy)phenyl-N'-(3-(1-isobutylpiperidin-4-yl) benzothien-5-yl)thiourea;

N-(4-butoxy)phenyl-N'-(3-piperidin-4-yl)benzothi-en-5-yl)thiourea;

N-(3,4-difluoro)phenyl-N'-(3-(1-butylpiperidin-4-yl) benzothien-5-yl)thiourea;

N-(3-fluoro-5-chloro)phenyl-N'-(3-(1-(2-pentyl) piperidin-4-yl)benzothien-5-yl)thiourea;

N-(3-phenpropyl)-N'-(3-(1-(sec-butyl)piperidin-4-yl) benzothien-5-yl)thiourea;

N-(4-trifluoromethyl)phenyl-N'-(3-(1-neopentylpiperidin-4-yl)benzothien-5-yl)thiourea;

N-(4-phenyl)phenyl-N'-(3-(1-pentylpiperidin-4-yl) benzothien-5-yl)thiourea;

N-hexyl-N'-(3-(1-propylpiperidin-4-yl)benzothien-5-yl) urea;

N-(2-penten-5-yl)-N'-(3-(1-(sec-butyl)piperidin-4-yl) benzothien-5-yl)urea;

N-(1-hexen-6-yl)-N'-(3-(1-pentylpiperidin-4-yl) benzothien-5-yl)urea;

N-(3-hexen-6-yl)-N'-(3-(1-(3-pentyl)piperidin-4-yl) benzothien-5-yl)urea;

N-cyclopropyl-N'-(3-(1-hexylpiperidin-4-yl)benzothien-5-yl)urea;

N-cyclooctyl-N'-(3-(1-(tert-butyl)piperidin-4-yl) benzothien-5-yl)urea;

N-(3-iodo)phenyl-N'-(2-methyl-3-(1-butylpiperidin-4-yl) benzothien-5-yl)urea;

N-(3-phenyl)phenyl-N'-(3-(1-propylpiperidin-4-yl) benzothien-5-yl)urea;

N-(3-propoxy)phenyl-N'-(3-(1-(2-pentyl)piperidin-4-yl) benzothien-5-yl)urea;

N-(2-formyl)phenyl-N'-(3-(1-(3-pentyl)piperidin-4-yl) benzothien-5-yl)urea;

N-(3-acetyl)phenyl-N'-(3-(1-(2-pentyl)piperidin-4-yl) benzothien-5-yl)urea phenylpropionate;

N-(3-propanoyl)phenyl-N'-(3-(1-pentylpiperidin-4-yl) benzothien-5-yl)urea;

N-(2-ethylthio)phenyl-N'-(3-(1-(3-pentyl)piper-idin-4-yl) benzothien-5-yl)urea;

N-(3-isopropylthio)phenyl-N'-(3-(1-isopropylpiperidin-4-yl)benzothien-5-yl)urea

N-(3-isopropyl)phenyl-N'-(3-(1-isopropylpiperidin-4-yl) benzothien-5-yl)urea;

N-(2-butyl)phenyl-N'-(3-(1-butylpiperidin-4-yl) benzothien-5-yl)urea;

N-(3-propoxycarbonyl)phenyl-N'-(3-(1-isobutylpiperidin-4-yl)benzothien-5-yl)urea;

N-(2,4-diiodo)phenyl-N'-(3-(1-(sec-butyl)piper-idin-4-yl)benzothien-5-yl)urea;

N-(3-fluoro-5-chloro)phenyl-N'-(3-(1-(2-pentyl) piperidin-4-yl)benzothien-5-yl)urea;

N-(3-phenpropyl)-N'-(3-(1-propylpiperidin-4-yl) benzothien-5-yl)urea;

N-ethyl-N-phenyl-N'-(3-(1-butylpiperidin-4-yl) benzothien-5-yl)urea;

N-isopropyl-N-phenyl-N'-(3-(1-(sec-butyl)piperi-din-4-yl)benzothien-5-yl)urea;

N-ethyl-N-butyl-N'-(3-(1-(2-pentyl)piperidin-4-yl) benzothien-5-yl)urea;

N-propyl-N-isopropyl-N'-(3-(1-isobutylpiperidin-4-yl)benzothien-5-yl)urea;

N,N-diisopropyl-N'-(3-(1-butylpiperidin-4-yl)benzothien-5-yl)urea;

N,N-dibutyl-N'-(3-(1-butylpiperidin-4-yl)benzothien-5-yl)urea;

5-butoxycarbonylamino-3-(1-propylpiperidin-4-yl)-2-propylbenzothiophene;

5-(1-hexen-6-yloxy)carbonylamino-3-(1-pentylpiperidin-4-yl)benzothiophene;

5-(3-hexen-6-yloxy)carbonylamino-3-(1-(3-pentyl)piperidin-4-yl)benzothiophene;

5-(2-fluorophenoxy)carbonylamino-3-(1-butylpiperidin-4-yl)benzothiophene;

5-(3-chlorophenoxy)carbonylamino-3-(1-hexylpiperidin-4-yl)benzothiophene;

5-(4-propoxyphenoxy)carbonylamino-3-(1-(sec-butyl)piperidin-4-yl)benzothiophene;

5-cyclopropoxycarbonylamino-3-(1-(tert-butyl)piperidin-4-yl)benzothiophene;

5-cyclooctyloxycarbonylamino-3-(1-isopropylpiperidin-4-yl)benzothiophene;

5-(4-methoxybutoxy)carbonylamino(1-ethylpiperidin-4-yl)benzothiophene;

5-(propanoyl)amino-3-(1-neopentylpiperidin-4-yl)benzothiophene mandalate;

5-(2-methylpropanoyl)amino-3-(1-(3-pentyl)piperidin-4-yl)benzothiophene;

5-(2-methyl-4-butyn-1-oyl)amino-3-(1-(tert-butyl)piperidin-4-yl)benzothiophene;

5-(2-methylbutanoyl)-N-methylamino-3-(1-ethylpiperidin-4-yl)benzothiophene;

5-(hex-3-enoyl)amino-3-(1-propylpiperidin-4-yl)benzothiophene;

5-(cyclohexaneacetyl)amino-3-(1-isopropylpiperi-din-4-yl)benzothiophene;

5-(cycloheptylcarbonyl)amino-3-(1-butylpiperidin-4-yl)benzothiophene;

5-(5-phenylpentanoyl)amino-3-(1-(2-pentyl)piperidin-4-yl)benzothiophene;

5-(5-phenoxypentanoyl)amino-3-(1-neopentylpiperidin-4-yl)benzothiophene;

5-(3-propoxypropanoyl)amino-3-(1-isopropylpiperidin-4-yl)benzothiophene;

5-(5-methoxypentanoyl)amino-3-(1-isopropylpiperidin-4-yl)benzothiophene;

5-((3-propoxycarbonyl)propanoyl)amino-3-(1-isobutylpiperidin-4-yl)benzothiophene;

5-((5-methoxycarbonyl)pentanoyl)amino-3-(1-isopropylpiperidin-4-yl)benzothiophene;

5-(N-benzoyl-N-ethyl)amino-3-(1-ethylpiperidin-4-yl)benzothiophene;

5-benzoylamino-3-(1-neopentylpiperidin-4-yl)benzothiophene;

5-(4-fluorobenzoyl)amino-3-(1-hexylpiperidin-4-yl)benzothiophene;

5-(2-chlorobenzoyl)amino-3-(1-neopentylpiperidin-4-yl)benzothiophene;

5-(2-bromobenzoyl)amino-3-(1-butylpiperidin-4-yl)benzothiophene;

5-(2-ethylbenzoyl)amino-3-(1-isobutylpiperidin-4-yl)benzothiophene;

5-(4-butylbenzoyl)amino-3-(1-methylpiperidin-4-yl)benzothiophene;

5-(2-propoxybenzoyl)amino-3-(1-(tert-butyl)piperidin-4-yl)benzothiophene;

5-(4-hexyloxybenzoyl)amino-3-(1-(3-pentyl)piperidin-4-yl)benzothiophene;

5-(2-ethylthiobenzoyl)amino-3-(1-ethylpiperidin-4-yl)benzothiophene;

5-(3-nitrobenzoyl)amino-3-(1-isobutylpiperidin-4-yl)benzothiophene;

5-(3-cyanobenzoyl)amino-3-(1-(2-pentyl)piperidin-4-yl)benzothiophene;

5-(4-(dimethylamino)benzoyl)amino-3-(1-isobutylpiperidin-4-yl)benzothiophene;

5-(3-(dibutylamino)benzoyl)amino-3-(1-methylpiperidin-4-yl)benzothiophene;

5-(4-trifluoromethoxybenzoyl)amino-3-(1-isopropylpiperidin-4-yl)benzothiophene;

5-(2-(formyl)benzoyl)amino-3-(1-neopentylpiperi-din-4-yl)benzothiophene;

5-(2-(acetyl)benzoyl)amino-3-(1-(3-pentyl)piperidin-4-yl)benzothiophene;

5-(3-(propanoyl)benzoyl)amino-3-(1-pentylpiperi-din-4-yl)benzothiophene;

5-(3-(butanoyl)benzoyl)amino-3-(1-methylpiperidin-4-yl)benzothiophene;

5-(2-(benzoyl)benzoyl)amino-3-(1-pentylpiperidin-4-yl)benzothiophene;

5-(2-(methanesulfonyl)benzoyl)amino-3-(1-butylpiperidin-4-yl)benzothiophene;

5-(2-butanesulfonylbenzoyl)amino-3-(1-isopropylpiperidin-4-yl)benzothiophene;

5-(3-phenylbenzoyl)amino-3-(1-(tert-butyl)piperidin-4-yl)benzothiophene;

5-(2,3-dibromo)benzoyl-N-isopropylamino-3-(1-isopropylpiperidin-4-yl)benzothiophene;

5-(2,4-diiodo)benzoylamino-(3-(1-(sec-butyl)piperidin-4-yl)benzothiophene;

5-(2-chloro-5-iodo)benzoylamino-(3-(1-hexylpiperidin-4-yl)benzothiophene;

5-(2-fluoro-6-iodo)benzoylamino-(3-(1-(tert-butyl)piperidin-4-yl)benzothiophene;

5-(2-thienoyl)amino-3-(1-(sec-butyl)piperidin-4-yl)benzothiophene;

5-(3-thienoyl)amino-3-(1-hexylpiperidin-4-yl)benzothiophene;

5-(2-furoyl)amino-3-(1-ethylpiperidin-4-yl)benzothiophene;

5-(2-furoyl)amino-3-(1-(3-pentyl)piperidin-4-yl)benzothiophene;

5-(2-furoyl)amino-3-(1-hexylpiperidin-4-yl)benzothiophene;

5-(3-furoyl)amino-3-(1-ethylpiperidin-4-yl)benzothiophene;

5-(3-furoyl)amino-3-(1-isopropylpiperidin-4-yl)benzothiophene;

5-(3-furoyl)amino-3-(1-(tert-butyl)piperidin-4-yl)benzothiophene;

5-(3-furoyl)amino-3-(1-pentylpiperidin-4-yl)benzothiophene;

5-(3-furoyl)amino-3-(1-(3-pentyl)piperidin-4-yl)benzothiophene;

N-[imidazol-4-yl]-5-carboxamido-3-(1-methylpiperidin-4-yl)benzothiophene;

N-[pyrimidin-5-yl]-5-carboxamido-3-(1-methylpiperidin-4-yl)benzothiophene;

N-[indol-2-yl]-5-carboxamido-3-(1-methylpiperidin-4-yl)benzothiophene;

N-[isoxazol-5-yl]-5-carboxamido-3-(1-methylpiperidin-4-yl)benzothiophene.

The synthetic methodology required to prepare the compounds of the invention is well known to those skilled in the art. A suitable electrophile is reacted with an appropriate 5-aminobenzothiophene or 5-aminobenzofuran to provide the corresponding ureas, thioureas, sulfonamides, carbamates and carboxamides of the present invention. This chemistry is illustrated in Synthetic Scheme I where X, Z, R, $R^4$, $R^5$, $R^6$, $R^7$ and $R^8$ are as described supra.

vinylpyridine. If necessary, an excess of the isocyanate, isothiocyanate, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polysty-rene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystal-

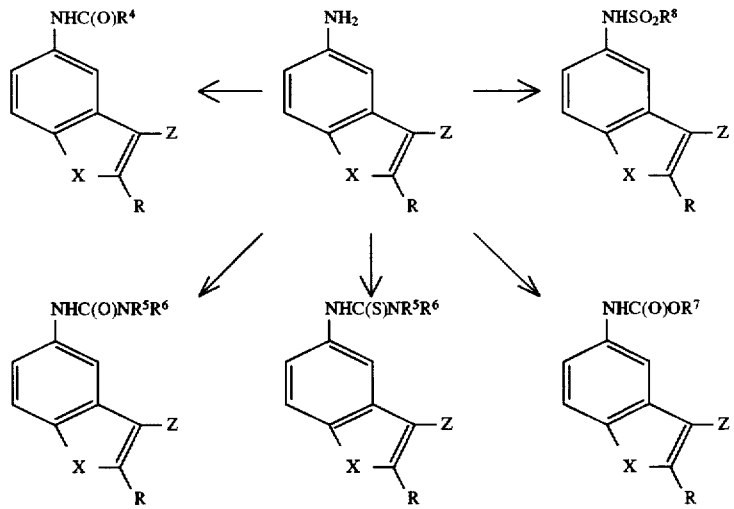

Synthetic Scheme I

To prepare compounds of the invention where Y is $R^8SO_2NH$—, a solution of the appropriate 5-aminobenzofuran or 5-aminobenzothiophene in a suitable solvent, such as tetrahydrofuran, dioxane, diethyl ether or dimethylformamide, at a temperature from about ambient to about 0° C., is reacted with a commercially available $R^8$-sulfonyl halide or $R^8$-sulfonic anhydride in the presence of a suitable base such as pyridine or triethylamine. The resultant sulfonamide may be isolated by dilution of the reaction mixture with water, adjustment of pH, and extraction with a water immiscible solvent such as dichloromethane. The product may be used for further reaction as recovered, or may be purified by chromatography, or by recrystallization from a suitable solvent.

Compounds of the invention where Y is —NHC(Q)$NR^5R^6$ are prepared by treating a solution of the appropriate 5-aminobenzofuran or 5-aminobenzothiophene in a suitable solvent, such as chloroform or dichloro-methane, with an appropriate isocyanate, isothio-cyanate, carbamoyl chloride or carbamoyl bromide. Appropriate carbamoyl chlorides are available by treating an amine of formula HN$R^5R^6$ with phosgene. When a carbamoyl chloride or carbamoyl bromide is used, the reactions are performed in the presence of a suitable base. Suitable bases include amines typically used as acid scavengers, such as pyridine or triethylamine, or commercially available polymer bound bases such as polylized from a suitable solvent if desired. The skilled artisan will appreciate that compounds of the invention which are ureas may be converted into the corresponding thiourea by treatment with [2,4-bis(4-methoxyphenyl)-1,3-dithia-2,4-diphosphetane-2,4-disulfide] (Lawesson's Reagent) or phosphorus pentasulfide.

Compounds of the invention where Y is $R^4C(O)NH$— or —NHC(O)$OR^7$ are prepared by treating the desired 5-aminobenzofuran or 5-aminobenzothiophene with either an appropriate carboxylic acid chloride, bromide or anhydride, or an appropriately substituted chloroformate optionally in the presence of an acylation catalyst such as dimethylaminopyridine, in the presence of a suitable base. Suitable bases include amines typically used as acid scavengers, such as pyridine or triethylamine, or commercially available polymer bound bases such as polyvinylpyridine. When an excess of the electrophile is necessary to ensure complete reaction of the amine, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture to remove the polymer bound constituents, and then concentration of the filtrate under reduced pressure to isolate the desired product. The product from these reactions may be purified chromatographically or recrystallized from a suitable solvent if desired.

Alternatively, compounds of the invention where Y is R⁴C(O)NH— may be prepared by reacting the 5-aminobenzofuran or 5-aminobenzothiophene with an appropriate carboxylic acid in the presence of a typical peptide coupling reagent such as N,N'-carbonyldiimidazole (CDI), N,N'-dicyclohexylcarbodiimide (DCC) and 1-(3-dimethylaminopropyl)-3-ethylcarbodiimide hydrochloride (EDC). Polymer supported forms of carbodiimide peptide coupling reagents are useful for the preparation of compounds of the present invention. A polymer supported form of EDC, for example, has been described (*Tetrahedron Letters*, 34(48), 7685 (1993)). Additionally, a new carbodiimide coupling reagent, 1-(3-(1-pyrrolidinyl)-propyl)-3-ethylcarbodiimide (PEPC), and its corresponding polymer supported forms have been discovered and are very useful for the preparation of the compounds of the present invention.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethylphenylacetamidomethyl resin (Pam Resin) and 4-benzyloxybenzyl alcohol resin (Wang Resin) available from Advanced Chemtech of Louisville, Ky. (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis. (see Aldrich 1994–1995 catalog, page 899).

Methods for the preparation of PEPC and its polymer supported forms are outlined in the following scheme.

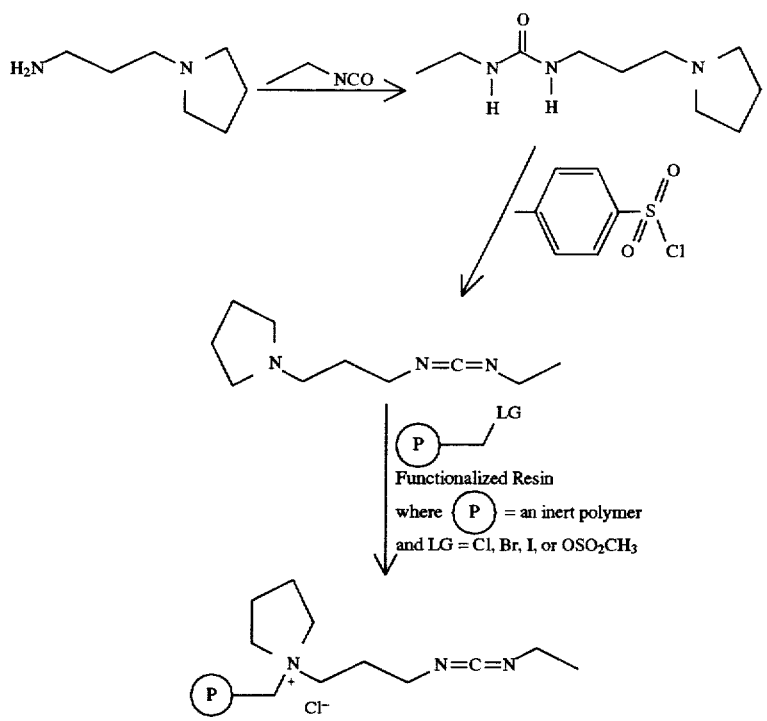

Briefly, PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient to about 45° C., for from about three hours to about three days. Typically, the product may be isolated by washing the reaction with water and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

The 5-aminobenzofurans and 5-aminobenzothiophenes required for the preparation of the compounds of the present invention may be prepared by methods well known to one of ordinary skill in the art. Compounds of the invention where X is O and Z is moiety (b) are 5-substituted-3-(2- aminoethyl)benzofurans. These compounds are derived from the corresponding 5-aminobenzofurans which may be prepared by the procedure described in Synthetic Scheme II where "amine" is —NR²R³ or phthalimidyl, and R, R² and R³ are as previously defined.

chromatography or fractional crystallization at any convenient point in the synthesis. The 5-nitrobenzofuran (i) is then subjected to hydrogenation over platinum on carbon in a suitable solvent, typically a lower alkanol, under standard conditions, to provide the desired 5-aminobenzofuran (ii).

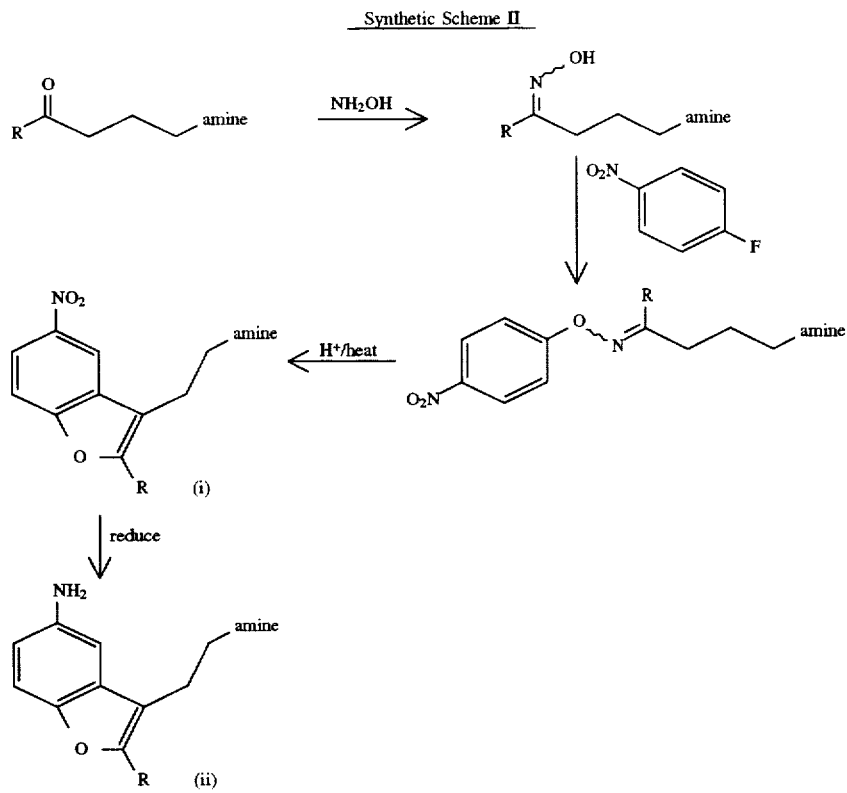

Synthetic Scheme II

An appropriate aminoketone and hydroxylamine hydrochloride are combined in an appropriate solvent, typically water or a lower alkanol such as methanol or ethanol. The resulting mixture is treated with a suitable base, typically potassium or sodium carbonate, pyridine or triethylamine, and the reaction mixture heated to reflux until all of the starting aminoketone has reacted. The resulting oxime may then be used directly or purified by crystallization or chromatography. The resulting oxime and 4-nitrofluorobenzene are combined in an appropriate solvent, for example tetrahydrofuran, dimethylformamide or N-methylpyrrolidin-one. This mixture is then treated with a suitable base, such as sodium or potassium hydride, and the reaction mixture warmed in the range of from about 0° C. to about 70° C., optionally in the presence of a crown ether, until the oxime is consumed. The resulting O-substituted oxime is isolated by normal extractive workup and may be purified, if necessary or desired, by crystallization or chromatography. The O-substituted oxime is then treated with an acid such as formic acid, or an acid mixture such as hydrogen chloride in a lower alkanol, to provide the desired 5-nitro-3-(2-aminoethyl)benzofuran. The reaction may be performed at a temperature from about room temperature to about the reflux temperature of the reaction solvent. The resulting compound is isolated by normal extractive workup and may be purified by crystallization or chromatography. The skilled artisan will appreciate that where R is $C_1$-$C_4$ alkyl, the ring closure step will result in two possible isomeric products. These compounds may be separated by The 5-nitrobenzofurans (i) and 5-aminobenzofurans (ii) are novel and represent further embodiments of the present invention.

The aminoketones required for the synthesis of the compound of the present invention are available by methods well known to the skilled artisan. One method is to react an appropriate haloketone, optionally protected as the corresponding ketal, with an appropriate amine or phthalimidate salt under standard alkylating conditions as described in Synthetic Scheme III, where halo is chloro, bromo or iodo and R, R² and R³ are as defined supra.

Synthetic Scheme III

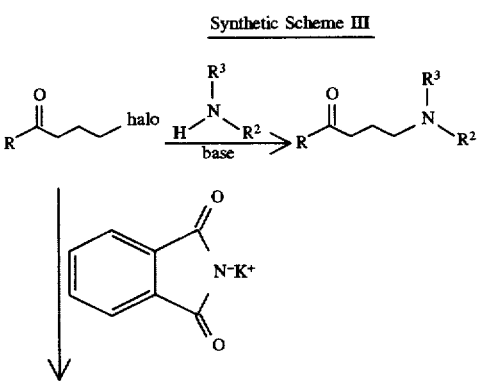

-continued
Synthetic Scheme III

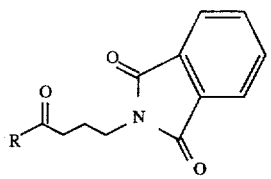

The haloketone and an appropriate amine are combined in a suitable solvent. such as acetonitrile. dichloromethane. acetone or dimethylformamide, in the presence of a suitable base, such as potassium or sodium carbonate. The skilled artisan will appreciate that when the haloketone is reacted with a phthalimidate salt. however, no additional base is required. The resulting mixture is heated to a temperature from about 40° C. to about 120° C. until all reactants are consumed. These reactions typically require about 2 hours to about 3 days to reach completion. The desired aminoketones may be isolated by filtering the reaction mixture to remove any solids which have formed, and concentrating the reaction mixture under reduced pressure. Alternatively, the reaction mixture may be partitioned between water and a water immiscible solvent such as dichloromethane. The water immiscible phase is then concentrated under reduced pressure to provide the desired compound. The aminoketones isolated in this manner may be used directly in a subsequent step or purified by distillation. chromatography, or crystallization from a suitable solvent if desired.

The 5-substituted-3-(2-aminoethyl)benzofurans of the present invention where $R^2$ is benzyl or 1-phenylethyl, while useful as 5-HT$_{1F}$ agonists, are also useful intermediates for the preparation of other compounds of the invention. When subjected to hydrogenation conditions in the presence of palladium, the $R^2$ moiety is removed by hydrogenolysis to give the corresponding secondary amines. These secondary amines may then be alkylated with an appropriate alkylating agent under the alkylation conditions described supra, or they may be subjected to reductive alkylation conditions in the presence of an appropriate aldehyde, to provide additional compounds of the invention. Furthermore, the phthalimides described supra may be treated with hydrazine to provide the corresponding primary amines. These primary amines may be subjected to sequential reductive alkylations to provide the compounds of the present invention. This chemistry is illustrated in Synthetic Scheme IV where $R^{2'}$—CHO represents an aldehyde which, after undergoing the reductive alkylation reaction provides the moiety $R^2$. and R. $R^2$, $R^3$ and Y are as defined supra.

Synthetic Scheme IV

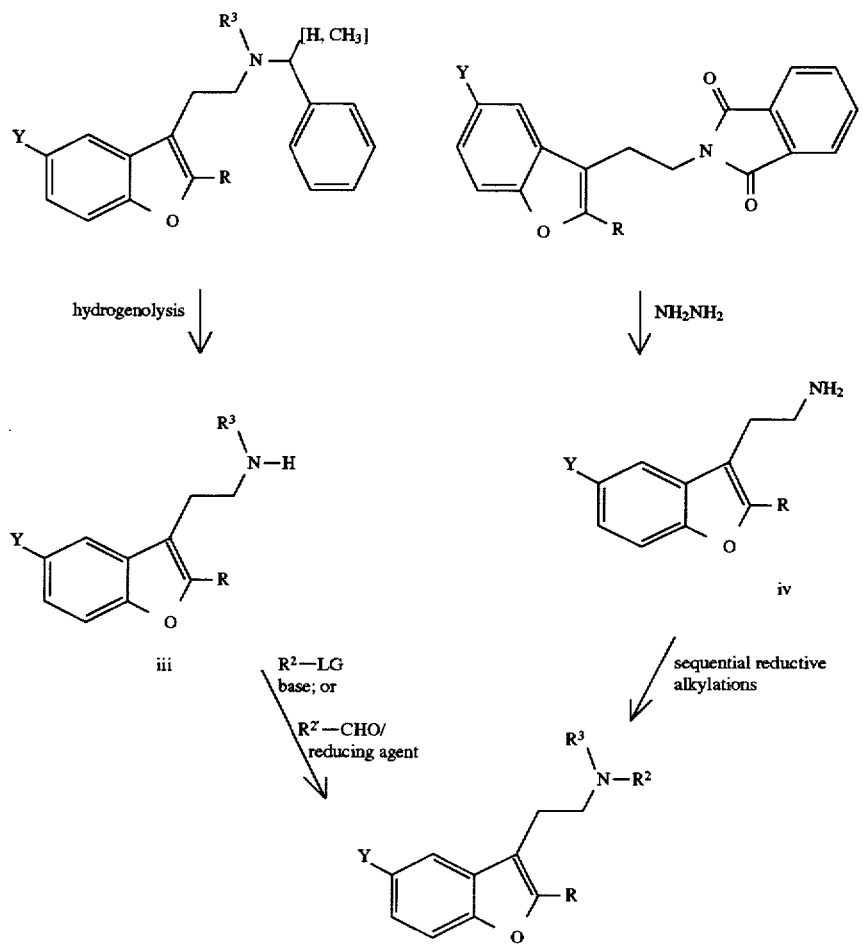

The reductive alkylation may be performed by combining an appropriate aldehyde, for example R²'—CHO, with the secondary amine (iii) or primary amine (iv) in a suitable solvent. Suitable solvents include tetrahydro-furan, dichloromethane, and the lower alkanols such as methanol, ethanol or isopropanol. The preferred solvents for the reductive alkylation include methanol and dichloromethane. The aldehyde and amine are typically combined in the presence of an acid, such as acetic acid or hydrogen chloride, and a hydride reducing agent. Suitable hydride reducing agents include sodium borohy-dride, sodium cyanoborohydride or sodium triacetoxyboro-hydride. Preferred hydride reducing agents include sodium cyanoborohydride or sodium triacetoxyborohydride. The combined reagents are allowed to react at a temperature of from about ambient to the reflux temperature of the solvent. The reaction time is typically from about 3 to about 24 hours. The compounds of the invention may then be isolated and purified by standard extractive workups. The compounds may be further purified by chromatography or crystallization from suitable solvents if desired.

The skilled artisan will appreciate that reductive alkylations of the primary amine (iv) may be performed sequentially. One equivalent of a first aldehyde is used to prepare the corresponding secondary amine under standard reductive alkylation procedures. This secondary amine may be isolated if desired or treated directly with a second aldehyde under the reductive alkylation conditions described supra. When $R^1$ and $R^2$ are to be the same, the primary amine may be exhaustively alkylated if desired.

The skilled artisan will also appreciate that, as an alternative to the reductive alkylation conditions described supra, the aldehyde and amine may be combined in a suitable solvent in the presence of acid. The resulting imine may then be reduced in a separate step by addition of a suitable hydride reducing agent, or by subjecting the reaction mixture to hydrogenation conditions using standard precious metal catalysts. The use of hydrogenation conditions is limited to those compounds of the invention which are stable to the reaction conditions. The skilled artisan will also appreciate that while the reductive alkylation procedures described supra describe the use of aldehydes, ketones may also be used to prepare other compounds of the invention.

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of this invention. The specific alkylating agent employed is determined by its commercial availability or a convenient synthesis from commercially available starting materials. The preferred alkylating agents for synthesis of compounds of this invention are those where the leaving group is chloro, bromo or methanesulfonyloxy.

Alkylating agents required to prepare compounds where $R^2$ is aryl-($C_1$-$C_3$ alkylene) or heteroaryl-($C_1$-$C_3$ alkylene), if not commercially available, are prepared from the corresponding alcohol by standard methods. The preparation of the required alkylating agents from the corresponding alcohols and the preparation of certain of the alcohols themselves are described in U.S. Pat. No. 5,521,196, herein incorporated by reference.

Compounds of the invention where X is S and Z is moiety (b) are 5-substituted-3-(2-aminoethyl)benzothiophenes. These compounds are derived from the corresponding 5-aminobenzothiophenes which may be prepared by the procedure described in Synthetic Scheme V where $R^2$ and $R^3$ are as previously defined.

Synthetic Scheme V

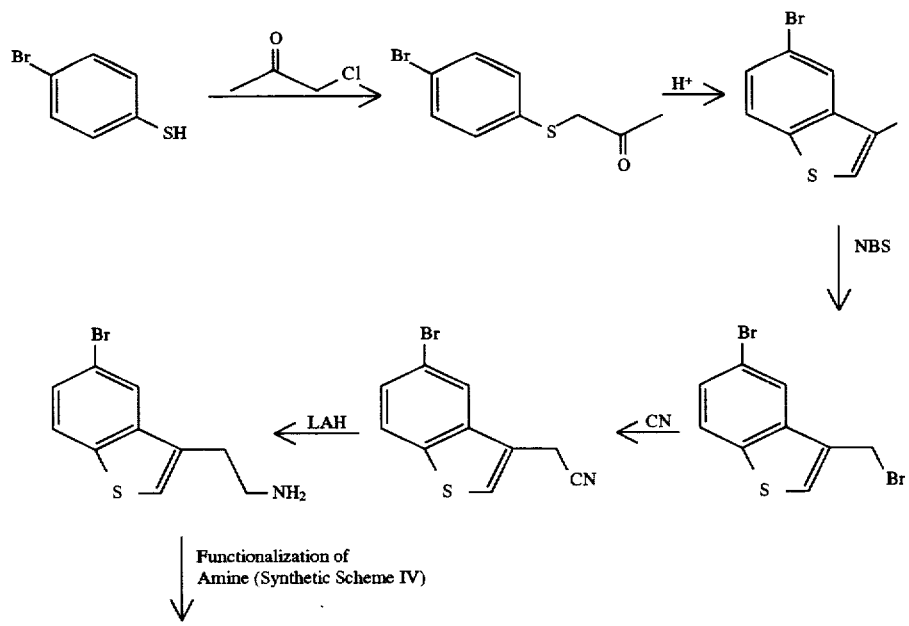

Synthetic Scheme V -continued

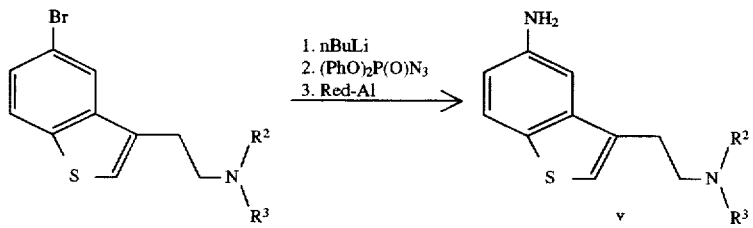

4-Bromothiophenol is alkylated with chloroacetone and the resulting thioether is cyclized under dehydrating acidic conditions to provide 5-bromo-3-methylbenzothiophene. The 3-methyl moiety is monobrominated with N-bromosuccinimide (NBS) and the corresponding nitrile prepared by nucleophilic displacement with cyanide to provide 5-bromo-3-cyanomethylbenzothiophene. This nitrile is reduced with lithium aluminum hydride (LAH) in diethyl ether to provide 5-bromo-3-(2-aminoethyl)benzo-thiophene. The primary amine is functionalized under the conditions described in Synthetic Scheme IV supra. The 5-amino substituent is introduced by first treating the corresponding 5-bromobenzothiophene with n-butyllithium, treating the resulting anion with diphenylphosphoryl azide to provide the corresponding azide and, finally, reducing the corresponding 5-azidobenzothiophene with sodium bis(2-methoxyethoxy)aluminum hydride (Red-Al) to provide the amine (v). The 5-substituted-3-(2-aminoeth-yl) benzothiophenes of the present invention are then prepared by subjecting the amine (v) to the reaction conditions described in Synthetic Scheme I. The 5-amino-3-(2-aminoethyl)benzothiophenes (v) are novel and represent a further embodiment of the present invention.

The 5-substituted-3-(2-aminoethyl)benzothiophenes of the present invention where R is $C_1$–$C_4$ alkyl are prepared as described in Synthetic Scheme VI where Y, $R^2$ and $R^3$ are as previously defined, and R' is $C_1$–$C_4$ alkyl.

Synthetic Scheme VI

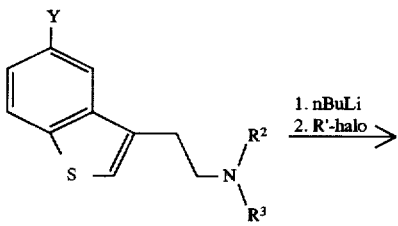

-continued
Synthetic Scheme VI

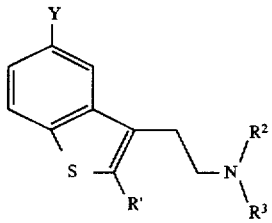

The 5-substituted-3-(2-aminoethyl)benzothiophene in a suitable solvent, such as tetrahydrofuran or diethyl ether, is treated with n-butyllithium. The resultant anion is quenched with an appropriate $C_1$–$C_4$ alkyl halide, preferably and alkyl bromide or alkyl iodide, and the desired product isolated by an extractive workup.

Compounds of the invention where X is O and Z is moiety (a) are 5-substituted-3-(piperidin-4-yl)benzofur-ans. Compounds of the invention where X is S and Z is moiety (a) are 5-substituted-3-(piperidin-4-yl)benzothio-phenes. These compounds are derived from the correspond-ing 5-aminobenzofurans and 5-aminobenzothiophenes respectively, which may be prepared by the procedure described in Synthetic Scheme VII where halide is chloro or bromo, $R^{1'}$ is benzyl or $C_1$–$C_4$ alkyl, and R and X are as previously defined.

Synthetic Scheme VII

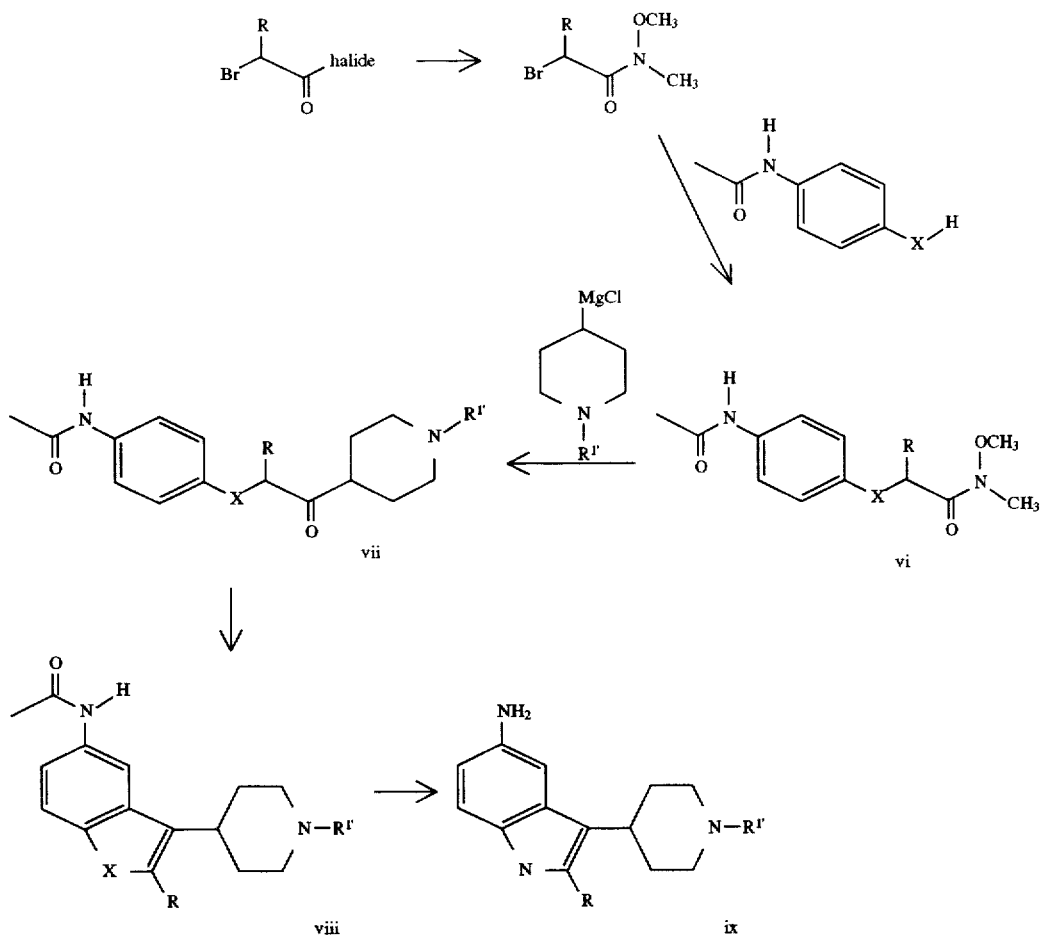

Bromoacetyl chloride or bromide is reacted with N-methoxy-N-methylamine under standard conditions to provide the corresponding bromoacetamide. The bromoacetamide is reacted with either N-acetyl-4-aminophenol or N-acetyl-4-aminothiophenol under standard alkylating conditions to provide the corresponding ether or thioether (vi). This thioether is reacted with an appropriate 1-substituted-piperidine-4-magnesium chloride, bromide or iodide to provide the ketone (vii). The necessary Grignard reagents may be prepared from the commercially available 4-halo-1-substituted-piperidines by reaction with magnesium in diethyl ether or tetrahy-drofuran under standard conditions. The N-acetyl-5-amino-3-(1-substituted-piperidin-4-yl) benzofurans or benzothiophenes (viii) are prepared by heating the ketone (vii) in the presence of an acid, typically polyphosphoric acid or sulfuric acid. While the acetamide moiety is typically hydrolyzed during the cyclization step, the desired 5-aminobenzothiophene or 5-aminobenzofuran (ix) may prepared in a separate hydrolysis step if necessary. The 5-aminobenzothiophenes and 5-aminobenzofurans of structure (ix) are novel and represent a further embodiment of the present invention.

The α-halo acid halides required for the preparation of the compounds of the invention are either commercially available or may be prepared from the corresponding acids or acid halides by methods well known to one of ordinary skill in the art. This chemistry is reviewed by Larock (*Comprehensive Organic Transformations*, pages 378–379, VCH Publishers, New York, 1989) The skilled artisan will appreciate that compounds of the invention where $R^1$ is H may be prepared by first subjecting the compound of formula (ix) where $R^{1'}$ is benzyl to the reaction conditions described in Synthetic Scheme I to introduce the appropriate moiety Y. Subjecting this compound to the hydrogenation conditions described supra provides the desired secondary amine. These secondary amines, while useful compounds of the invention in their own right, may be subjected to standard alkylation conditions to provide the corresponding tertiary amines of the present invention as desired.

The following preparations and examples further illustrate the synthesis of the compounds of this invention, and are not intended to limit the scope of the invention in any way. The compounds described below were identified by various standard analytical techniques as stated in the individual preparations and examples.

The aminoketones required for the synthesis of the compounds of the invention are available by the procedures described in Preparations I–III.

PREPARATION I

N,N-dimethyl-5-amino-2-pentanone

A mixture of 21.77 gm (180.5 mMol) 5-chloro-2-pentanone, 13.40 gm (164.3 mMol) dimethylamine hydrochloride and 50.0 gm (361.8 mMol) potassium carbonate in 150 mL acetonitrile was stirred at room temperature for 2 days and then at reflux for 2 hours. The reaction mixture was then cooled to room temperature and partitioned between water and dichloromethane. The phases were separated and the aqueous phase again extracted with dichloromethane. All organic phases were combined, dried over sodium sulfate and concentrated under reduced pressure. The residue was subjected to silica gel chromatography, eluting with dichloromethane containing 10% methanol and 1% ammonium hydroxide. Fractions shown to contain product were combined and concentrated under reduced pressure. The desired product was then isolated by distillation.

PREPARATION II

N-methyl-N-((S)-1-phenylethyl)-5-amino-2-pentanone

A mixture of 5.85 mL (38.87 mMol) 5-chloro-2-pentanone ethylene glycol ketal, 5.0 gm (37.0 mMol) N-methyl-(S)-1-phenylethylamine, 6.14 gm (37.0 mMol) potassium iodide and 15.33 gm (110.9 mMol) potassium carbonate in 100 mL acetonitrile was stirred at room temperature for 2 days. The reaction mixture was then filtered and the filtrate concentrated under reduced pressure. The residue was dissolved in 50 mL acetone to which was added 50 mL 2N hydrochloric acid. The resulting solution was stirred at room temperature for 3 hours and was then concentrated to half volume under reduced pressure. The residue was extracted with diethyl ether (2×50 mL) and the remaining aqueous solution was treated with 5N sodium hydroxide until the pH of the solution was about 13. This aqueous phase was now extracted with dichloromethane (3×60 mL). The organic phases were combined, dried over sodium sulfate and concentrated under reduced pressure. The residue was subjected to silica gel chromatography, eluting with 40% ethyl acetated in hexane. Fractions shown to contain product were combined and concentrated under reduced pressure to give 7.11 gm (88%) of the desired compound.

PREPARATION III 5-phthalimidyl-2-pentanone
5-phthalimidyl-2-pentanone ethylene glycol ketal A mixture of 25 gm (0.15 Mol) 5-chloro-2-pentanone ethylene glycol ketal, 42.2 gm (0.23 Mol) potassium phthalimidate, 150 mL ethanol and 150 mL dimethylformamide was heated at reflux for 3 days. The reaction mixture was cooled to room temperature, diluted with water and extracted with ethyl acetate. The organic extract was washed with water, dried over sodium sulfate and concentrated under reduced pressure to provide 36.8 gm (88%) of the desired ketal.

5-phthalimidyl-2-pentanone

A solution of 26.8 gm (97.2 mMol) 5-phthalimidyl-2-pentanone ethylene glycol ketal in 200 mL acetone and 200 mL 3N hydrochloric acid was stirred at room temperature for 14 hours. The reaction mixture was then adjusted to pH=12 with 50% sodium hydroxide and the acetone removed under reduced pressure. The remaining aqueous phase was extracted with ethyl acetate. This organic phase was washed with water, dried over sodium sulfate, and concentrated under reduced pressure to provide 15.8 gm (70%) of the desired ketone.

PREPARATION IV 5-amino-2-methyl-3-(N,N-dimethyl-2-aminoethyl) benzofuran dihydrochloride
N,N-dimethyl-5-amino-2-pentanone oxime A mixture of 20 gm (167 mMol) N,N-dimethyl-5-amino-2-pentanone, 14.5 gm (208 mMol) hydroxylamine hydrochloride, and 8.8 gm (83 mMol) sodium carbonate in 50 mL water was heated at reflux for 1.5 hours. After cooling to room temperature, the reaction mixture was extracted with dichloromethane. The organic extracts were combined, dried over sodium sulfate and concentrated under reduced pressure. The residual oil crystallized on standing at room temperature. The solid was washed with hexane to provide 12.8 gm (54%) of the desired oxime as a colorless solid in two crops.

N,N-dimethyl-5-amino-2-pentanone O-(4-nitrophenyl) oxime

A suspension of 15.0 gm (82 mMol) potassium hydride (22% dispersion in mineral oil) in 10 mL tetrahydrofuran was cooled in an ice bath. To this suspension was slowly added a solution of 9.8 gm (68 mMol) N,N-dimethyl-5-amino-2-pentanone oxime in 20 mL tetrahydrofuran resulting in vigorous gas evolution. Once this addition was complete, a solution of 12.5 gm (88.3 mMol) 4-nitrofluorobenzene and 0.90 gm (3.4 mMol) 18-crown-6 in 10 mL tetrahydrofuran were added. The dark solution was stirred for 1 hour at ice bath temperature and then for 3 hours at room temperature. The reaction mixture was then poured into 100 mL of aqueous 5% potassium carbonate and the resulting mixture was extracted with dichloromethane. These organic extracts were combined, washed with aqueous 5% potassium carbonate, dried over sodium sulfate and concentrated under reduced pressure. The residual oil was subjected to flash silica gel chromatography, eluting with 10% methanol in dichloromethane. Fractions containing product were combined and concentrated under reduced pressure to provide 7.3 gm (40%) of the desired oxime ether as a dark oil.

5-nitro-2-methyl-3-(N,N-dimethyl-2-aminoethyl) benzofuran

A solution of 7.3 gm (27 mMol) N,N-dimethyl-5-amino-2-pentanone O-(4-nitrophenyl)oxime in 100 mL ethanol was cooled in an ice bath and was then saturated with hydrogen chloride. The reaction mixture was heated at reflux for 4 hours and was then cooled to room temperature. After standing for 18 hours at room temperature the reaction mixture was concentrated under reduced pressure and the residue partitioned between dichloromethane and aqueous potassium carbonate. The phases were separated and the aqueous phase extracted with dichloromethane. The organic extracts were combined, dried over sodium sulfate and concentrated under reduced pressure. The residual oil was subjected to flash silica gel chromatography, eluting with 10% methanol in dichloromethane. Fractions containing the fastest eluting compound were combined and concentrated under reduced pressure to provide 4.2 gm (63%) of the desired 5-nitro-2-methyl-3-(N,N-dimethyl-2-aminoethyl) benzofuran. Fractions containing the slower eluting compound were combined and concentrated under reduced pressure to provide 1.4 gm (21%) of the isomeric 5-nitro-2-(N, N-dimethyl-4-aminobutyl)benzofuran.

Reduction of 5-nitro substituent

A mixture of 2.1 gm (8.6 mMol) 5-nitro-2-methyl-3-(N, N-dimethyl-2-aminoethyl)benzofuran and 0.5 gm platinum on carbon in tetrahydrofuran was hydrogenated at an initial hydrogen pressure of 60 p.s.i. at room temperature for 15 hours. The reaction mixture was filtered and the filtrate concentrated under reduced pressure. The residual oil was subjected to flash silica gel chromatography, eluting with dichloromethane containing 10% methanol and 1% ammonium hydroxide. Fractions containing product were combined and concentrated under reduced pressure to provide 1.42 gm (76%) 5-amino-2-methyl-3-(N,N-dimethyl-2-aminoethyl)benzofuran. The dihydrochloride salt was prepared and recovered as a light brown solid.

m.p.=150°–155° C.

PREPARATION V

N-[2-methyl-3-(N'-methyl-2-aminoethyl)benzofur-5-yl]-4-fluorobenzamide 5-amino-2-methyl-3-(N'-methyl-N'-benzyl-2-aminoethyl)benzofuran The title compound was prepared by subjecting N-methyl-N-benzyl-5-amino-2-pentanone, prepared by the procedure described in Preparation I, to the reaction conditions described in detail in Preparation IV.

N-[2-methyl-3- (N'-methyl-N'-benzyl-2-aminoethyl)benzofur-5-yl]-4-fluorobenzamide A mixture of 1.3 gm (4.4 mMol) 5-amino-2-methyl-3-(N'-methyl-N'-benzyl-2-aminoethyl)benzofuran, 0.73 gm (4.62 mMol) 4-fluorobenzoyl chloride, and 0.71 mL (8.8 mMol) pyridine in 50 mL dichloromethane was stirred at room temperature for 2 hours. The reaction mixture was then washed with water and the organic phase dried over sodium sulfate and then concentrated under reduced pressure. The residual oil was subjected to flash silica gel chromatography, eluting with a gradient of ethyl acetate containing from 50 to 0% hexane. Fractions containing product were combined and concentrated under reduced pressure to provide 1.76 gm (96%).

MS(m/e): 416(M$^+$)

Hydrogenolysis of benzyl group

A mixture of 0.34 gm (0.82 mMol) N-[2-methyl-3-(N'-methyl-N'-benzyl-2-aminoethyl)benzofur-5-yl]-4-fluorobenzamide, 0.52 gm (8.2 mMol) ammonium formate, and 0.050 gm 5% palladium on carbon in 20 mL methanol was heated at reflux for 1 hour. The reaction mixture was filtered hot and the filtrate concentrated under reduced pressure. The residual oil was subjected to flash silica gel chromatography, eluting with dichloromethane containing 10% methanol and 1% ammonium hydroxide. Fractions containing product were combined and concentrated under reduced pressure to provide 0.22 gm (80%) of the title compound.

m.p.=60°–65° C. MS(m/e): 326(M$^+$)

PREPARATION VI 5-amino-3-(N,N-dimethyl-2-aminoethyl)benzothiophene oxalate

S-(4-bromophenyl)-1-thio-2-pentanone

A mixture of 6.16 gm (32.6 mMol) 4-bromothiophenol, 2.59 mL (32.6 mMol) chloroacetone and 24 mL 2N aqueous sodium hydroxide in 150 mL tetrahydrofuran was stirred at room temperature for 2 hours. The reaction mixture was partitioned between water and 1:1 ethyl acetate:hexane. The organic phase was separated, dried over sodium sulfate, and concentrated under reduced pressure. The residual solid was used without further purification.

5-bromo-3-methylbenzothiophene

A solution of about 2 mL of polyphosphoric acid (PPA) in 60 mL chlorobenzene was heated to reflux. To this solution was added 1.0 gm (4.08 mMol) S-(4-bromophenyl)-1-thio-2-pentanone in portions over 20 minutes. The resulting mixture was then heated at reflux for 18 hours. The reaction mixture was then cooled to room temperature, the organic phase separated and concentrated under reduced pressure. The residual oil was subjected to flash silica gel chromatography, eluting with hexane containing 10% ethyl acetate. Fractions containing product were combined and concentrated under reduced pressure to provide 0.794 gm (86%) of the desired compound.

5-bromo-3-(bromomethyl)benzothiophene

A solution of 4.30 gm (18.9 mMol) 5-bromo-3-methylbenzothiophene, 0.25 gm (1.03 mMol) benzoylperoxide, and 3.37 gm (18.9 mMol) N-bromosuccinimide in 50 mL carbon tetrachloride was heated at reflux for 3 hours. The reaction mixture was cooled to room temperature, filtered and the filtrate concentrated under reduced pressure. The residue was subjected to flash silica gel chromatography, eluting with hexane. Fractions containing the desired compound were combined and concentrated under reduced pressure to provide 4.28 gm (74%) of the desired compound.

5-bromo-3-(cyanomethyl)benzothiophene

A mixture of 0.115 gm (2.34 mMol) sodium cyanide, 2 mL ethanol and 1 mL water was heated to reflux. To this refluxing mixture was added a solution of 0.356 gm (1.16 mMol) 5-bromo-3-(bromomethyl)benzothiophene in 4 mL ethanol. The resulting mixture was heated at reflux for 3 hours. The reaction mixture was cooled to room temperature and then partitioned between water and ethyl acetate. The phases were separated and the aqueous phase extracted with ethyl acetate. The combined organic phases were dried over sodium sulfate and concentrated under reduced pressure. The residue was subjected to flash silica gel chromatography, eluting with hexane containing 10% dichloromethane and 5% ethyl acetate. Fractions containing product were combined and concentrated under reduced pressure to provide 0.214 gm (73%) of the desired nitrile as a solid.

5-bromo-3-(2-aminoethyl)benzothiophene oxalate

A solution of 0.854 gm (3.4 mMol) 5-bromo-3-(cyanomethyl)benzothiophene in 25 mL diethyl ether was added to a suspension of 0.155 gm (4.08 mMol) lithium aluminum hydride (LAH) in 10 mL diethyl ether at a rate sufficient to maintain a gentle reflux. Once the addition was complete the reaction mixture was heated at reflux for 1 hour. The reaction mixture was then cooled to room temperature, diluted with 30 mL dichloromethane, and treated with sodium sulfate decahydrate to destroy excess LAH. After standing for 30 minutes at room temperature, the mixture was filtered and the filtrate concentrated under reduced pressure. The residue was subjected to flash silica gel chromatography, eluting with dichloromethane containing 10% methanol and 1% ammonium hydroxide. Fractions containing product were combined and concentrated under reduced pressure to provide 0.386 gm (44%) of the desired amine. The oxalate salt was prepared.

m.p.=230°–232° C.; MS(m/e): 256(M$^+$)

5-bromo-3-(N',N'-dimethyl-2-aminoethyl)benzothiophene oxalate

A mixture of 0.80 gm (0.31 mMol) 5-bromo-3-(2-aminoethyl)benzothiophene, 0.24 mL (3.03 mMol) formaldehyde (38% in water), 0.21 gm (1.0 mMol) sodium triacetoxyborohydride, and 0.14 mL (2.45 mMol) acetic acid in 10 mL dichloromethane was stirred at room temperature for 24 hours. The pH of the solution was adjusted to about 12 by the addition of 2N sodium hydroxide and the mixture extracted with dichloromethane. The organic phase was concentrated under reduced pressure and the residue subjected to flash silica gel chromatography, eluting with dichloromethane containing 10% methanol and 1% ammonium hydroxide. Fractions containing product were combined and concentrated under reduced pressure to provide 0.064 gm (73%) of 5-bromo-3-(N',N'-dimethyl-2-aminoethyl)benzothiophene. The oxalate salt was prepared. m.p.=183°–185° C.; MS(m/e): 284(M⁺)

5-amino-3-(N',N'-dimethyl-2-aminoethyl)benzothiophene oxalate

A solution of 0.193 gm (0.68 mMol) 5-bromo-3-(N',N'-dimethyl-2-aminoethyl)benzothiophene in 10 mL tetrahydrofuran was cooled to –78° C. and then to it were added 0.425 mL (0.68 mMol) n-butyllithium (1.6M in hexane). The reaction mixture was stirred at –78° C. for 10 minutes and then this solution was cannulated into a solution of 0.18 mL (0.83 mMol) diphenylphosphoryl azide in 10 mL tetrahydrofuran at –78° C. The reaction mixture was maintained at this temperature for 2 hours and then 1 mL (3.56 mmol) sodium bis(2-methoxyethoxy)aluminum hydride (Red-Al) was added and the reaction mixture warmed to 0° C. The reaction mixture was maintained at this temperature for 30 minutes and then at room temperature for 30 minutes. The reaction mixture was cooled again to 0° C. and water added to decompose excess hydride reagent. The pH of the solution was adjusted to about 12 by the addition of 2N sodium hydroxide and was then extracted first with ethyl acetate and then with dichloromethane. The combined organic extracts were dried over sodium sulfate and then concentrated under reduced pressure. The residue was subjected to flash silica gel chromatography, eluting with dichloromethane containing 6% methanol and 0.5% ammonium hydroxide. Fractions containing the desired product were combined and concentrated under reduced pressure to provide 0.027 gm (18%) of 5-amino-3-(N',N'-dimethyl-2-aminoethyl)benzothiophene. The oxalate salt was formed to provide the title compound.
m.p.=168°–170° C.

PREPARATION VII 5-amino-3-(piperidin-4-yl)benzofuran
N-methyl-N-methoxy 2-(4-acetamidophenoxy)acetamide To a stirred slurry of 6.00 gm (61.5 mMol) N,O-dimethylhydroxylamine hydrochloride in dichloromethane at 0° C. were added 6.6 mL (79.9 mMol) bromoacetyl chloride followed by 5 mL (61.5 mmol) pyridine. The reaction mixture was allowed to warm gradually to room temperature and then stirred for 2 hours. The volatiles were removed under reduced pressure and the residue partitioned between dichloromethane and saturated aqueous ammonium chloride. The organic phase was separated and the aqueous extracted again with dichloromethane. The organic extracts were combined, washed sequentially with water and saturated aqueous sodium chloride, dried over magnesium sulfate and concentrated under reduced pressure to provide 10.00 gm (89%) of N-methyl-N-methoxy 2-bromoacetamide.

This bromoacetamide was dissolved in acetonitrile and to the solution were added 10.75 gm (71.15 mMol) 4-acetamidophenol followed by 23.10 gm (71.1 mMol) cesium carbonate. The reaction mixture was heated at reflux for 3 hours and then concentrated under reduced pressure. The residue was partitioned between dichloromethane and 1N aqueous sodium hydroxide. The organic phase was separated, washed sequentially with water and saturated aqueous sodium chloride, dried over magnesium sulfate and concentrated under reduced pressure. The residue was subjected to silica gel chromatography, eluting with ethyl acetate. Fractions containing product were combined and concentrated under reduced pressure to provide 10.34 gm (74%) of the desired compound.

¹H-NMR(CDCl₃): δ 2.06(s, 3H), 3.20 (s,3H), 3.71 (s, 3H), 4.75 (s, 2H), 6.80 (d, J=10 Hz, 2H), 7.31 (d, J=10 Hz, 2H).

MS: m/e=253(M+1)
1-methyl-4-(2-(4-acetamidophenoxy)acetyl)piperidine

A crystal of iodine was added to 0.45 gm (18.7 mMol) magnesium turnings covered with 6 mL tetrahydrofuran. To this mixture were added 5–6 drops of dibromoethane and the mixture was heated with a heat gun to initiate the reaction. Once the iodine color disappeared, 2 mL (15 mMol) 1-methyl-4-chloropiperidine were added and heating continued for an additional 30 seconds. After the exothermic reaction no longer maintained reflux temperature, the reaction mixture was heated at reflux for 30 minutes and was then cooled to 0° C. To the cold mixture was added the previously prepared N-methyl-N-methoxy 2-(4-acetamidophenoxy)acetamide and the resulting mixture stirred for 30 minutes at 0° C. and then an additional hour after warming to room temperature. The reaction was quenched by the addition of water and the resulting mixture extracted well with ethyl acetate. The combined organic extracts were washed saturated aqueous ammonium chloride, dried over magnesium sulfate, and concentrated under reduced pressure. The resulting residue was subjected to silica gel chromatography, eluting with dichloromethane containing 5% methanol. Fractions shown to contain product were combined and concentrated under reduced pressure to provide 0.90 gm (47%) of the desired ketone.

MS: m/e 291(M+1)
Cyclization/amide hydrolysis

A mixture of 0.85 gm (3.1 mMol) 1-methyl-4-(2-(4-acetamidophenoxy)acetyl)piperidine and 8.5 gm polyphosphoric acid was heated at 170°–200° C. for 3 hours. The reaction mixture was cooled in an ice bath, diluted with water and the pH adjusted to about 9 with 2N sodium hydroxide. The aqueous was extracted well with chloroform. The combined organic extracts were washed sequentially with water and saturated aqueous sodium chloride, dried over sodium sulfate, and concentrated under reduced pressure. The residue was subjected first to ion exchange chromatography on a VARIAN BOND ELUT SCX™ (Varian, Harbor City, Calif., U.S.A.) ion exchange column (10 gm). The column was eluted with several volumes of methanol and eluted with 2M ammonia in methanol. Fractions from the column containing product were concentrated under reduced pressure and the residue from this column subjected to silica gel chromatography, eluting with dichloromethane containing 10% methanol and 1% ammonium hydroxide. Fractions from this column containing product were combined and concentrated under reduced pressure to provide 0.34 gm (47%) of the title compound.

¹H-NMR(CDCl₃): δ 1.74–2.25 (m, 6H), 2.31 (s, 3H), 2.55–2.63 (m, 1H), 2.92–3.01 (m, 2H), 3.46 (br s, 2H), 6.63 (dd, J=8.58 Hz, 2.25 Hz, 1H), 6.86 (d, J=2.25 Hz, 1H), 7.22 (d, J=8.58 Hz, 1H), 7.28 (s, 1H).

MS: m/e=231(M+1)

PREPARATION VIII 1-(3-(1-pyrrolidinyl)propyl)-3-ethylcarbodiimide (PEPC)
N-ethyl-N'-3-(1-pyrrolidinyl)proplylurea To a solution of 27.7 gm (0.39 mole) ethyl isocyanate in 250 mL chloroform were added 50 gm (0.39 mole) 3-(1-pyrrolidinyl)propylamine dropwise with cooling. Once the addition was complete, the cooling bath was removed and the reaction mixture stirred at room temperature for 4 hours. The reaction mixture was then concentrated under reduced pressure to give 74.5 gm (96.4%) of the desired urea as a clear oil.

1-(3-(1-pyrrolidinyl)propyl)-3-ethylcarbodiimide (PEPC)

To a solution of 31.0 gm (0.156 mole) N-ethyl-N'-3-(1-pyrrolidinyl)propylurea in 500 mL dichloromethane were added 62.6 gm (0.62 mole) triethylamine and the solution was cooled to 0° C. To this solution were then added 59.17 gm (0.31 mole) 4-toluenesulfonyl chloride in 400 mL dichloromethane dropwise at such a rate as to maintain the reaction at 0°–5° C. After the addition was complete, the reaction mixture was warmed to room temperature and then heated to reflux for 4 hours. After cooling to room temperature, the reaction mixture was washed with saturated aqueous potassium carbonate (3×150 mL). The aqueous phases were combined and extracted with dichloromethane. All organic phases were combined and concentrated under reduced pressure. The resultant orange slurry was suspended in 250 mL diethyl ether and the solution decanted off from the solid. The slurry/decantation process was repeated 3 more times. The ether solutions were combined and concentrated under reduced pressure to give 18.9 gm (67%) of the desired product as a crude orange oil. A portion of the oil was distilled under vacuum to give a colorless oil distilling at 78°–82° C. (0.4 mm Hg).

PREPARATION IX

Preparation of a polymer supported form of 1-(3-(1-pyrrolidinyl)propyl)-3-ethylcarbodiimide (PEPC)

A suspension of 8.75 gm (48.3 mMol) 1-(3-(1-pyrrolidinyl)propyl)-3-ethylcarbodiimide and 24.17 gm (24.17 mMol) Merrifield's resin (2% cross-linked, 200–400 mesh, chloromethylated styrene/divinylbenzene copolymer, 1 meq. Cl/gm) in dimethylformamide was heated at 100° C. for 2 days. The reaction was cooled and filtered and the resulting resin washed sequentially with 1L dimethylformamide, 1L tetrahydrofuran and 1L diethyl ether. The remaining resin was then dried under vacuum for 18 hours.

EXAMPLE 1

N-[3-(N',N'-dimethyl-2-aminoethyl)benzothien-5-yl]-4-fluorobenzamide oxalate

A mixture of 0.027 gm (0.12 mMol) 5-amino-3-(N',N'-dimethyl-2-aminoethyl)benzothiophene, 0.05 mL (0.42 mMol) 4-fluorobenzoyl chloride, and 0.10 mL (1.24 mMol) pyridine in 5 mL dichloromethane was stirred at room temperature for 2 hours. The reaction mixture was then partitioned between 2N sodium hydroxide and dichlorometh-ane. The organic phase was separated and the aqueous phase extracted again with dichloromethane. The combined organic phases were dried over sodium sulfate and concentrated under reduced pressure. The residue was subjected to flash silica gel chromatography, eluting with dichloromethane containing 10% methanol and 1% ammonium hydroxide. Fractions containing product were combined and concentrated under reduced pressure to provide 0.018 gm (44%) of N-[3-(N',N'-dimethyl-2-aminoethyl)benzothien-5-yl]-4-fluorobenzamide. The oxalate salt was formed to provide the title compound.

m.p.=121°–123° C.; MS(m/e): 342(M$^+$)

EXAMPLE 2

N-[2-methyl-3-(N',N'-dimethyl-2-aminoethyl)benzofur-5-yl]-4-fluorobenzamide

Beginning with 0.049 gm (0.23 mmol) 5-amino-2-methyl-3-(N',N'-dimethyl-2-aminoethyl)benzofuran, 0.055 gm (72%) of the title compound were prepared by the procedure described in detail in EXAMPLE 1.

m.p.=122°–125° C.; MS(m/e): 340(M$^+$)

EXAMPLE 3

N-[3-(1-methylpiperidin-4-yl)benzofur-5-yl]-4-fluorobenzamide

Beginning with 0.113 gm (0.49 mMol) 5-amino-3-(1-methylpiperidin-4-yl)benzofuran, 0.148 gm (85%) of the title compound were prepared by the procedure described in detail in EXAMPLE 1.

MS(m/e): 353(M+1)

EXAMPLE 4

N-[2-methyl-3-(N',N'-dimethyl-2-aminoethyl)benzofur-5-yl]-2-methyl-4-fluorobenzamide A mixture of 0.10 gm (0.46 mMol) 5-amino-2-methyl-3-(N',N'-dimethyl-2-aminoethyl)benzofuran, 0.085 gm (0.55 mMol) 2-methyl-4-fluorobenzoic acid, 0.074 gm (0.55 mMol) 1-hydroxybenzotriazole, and 0.105 gm (0.55 mMol) 1-(3-dimethylaminopropyl)-3-ethylcarbodiimide hydrochloride (EDCI) in 20 mL tetrahydrofuran was stirred at room temperature for 18 hours. The reaction mixture was partitioned between dichloromethane and 1N sodium hydroxide. The organic phase was separated, dried over sodium sulfate and concentrated under reduced pressure. The residue was subjected to flash silica gel chromatography, eluting with dichloromethane containing 10% methanol. Fractions containing product were combined and concentrated under reduced pressure to provide 0.11 gm (68%) of the title compound.

MS(m/e): 354(M$^+$)

General procedure for the coupling of carboxylic acid halides with 5-aminobenzofurans and benzothiophenes To a suspension of 2 equivalents of polymer bound 4-(N,N-dimethylamino)piperidine in chloroform are added 1 equivalent of the 5-aminobenzofuran or 5-aminobenzothiophene and 1.5 equivalents of the desired carboxylic acid halide. The reaction is agitated for 48 hours at room temperature. The reaction mixture is then loaded onto a VARIAN BOND ELUT SCX™ (Varian, Harbor City, Calif., U.S.A.) ion exchange column. The column is eluted with several volumes of methanol and is then eluted with either saturated methanolic hydrogen chloride or 2M ammonia in methanol. Fractions from the column containing product are concentrated under reduced pressure. Compounds eluted with methanolic hydrogen chloride provide the hydrochloride salts, and compounds eluted with ammonia in methanol provide the free bases, of compounds of the invention. This procedure is illustrated by Examples 5–10.

EXAMPLE 5

N-[2-methyl-3-(N',N'-dimethyl-2-aminoethyl)benzofur-5-yl]acetamide

Beginning with 10 mg (0.046 mMol) 5-amino-2-methyl-3-(N',N'-dimethyl-2-aminoethyl)benzofuran and 5.4 mg (0.069 mMol) acetyl chloride, 8.4 mg (70%) of the title compound were prepared.

MS(m/e): 261(M$^+$)

EXAMPLE 6

N-[2-methyl-3-(N',N'-dimethyl-2-aminoethyl)benzofur-5-yl]cyclopropanecarboxamide Beginning with 10 mg (0.046 mMol) 5-amino-2-methyl-3-(N',N'-dimethyl-2-aminoethyl)benzofuran and 7.2 mg (0.069 mMol) cyclopropanecarbonyl chloride, 10.5 mg (53%) of the title compound were prepared.

MS(m/e): 287(M⁺)

EXAMPLE 7

N-[2-methyl-3-(N',N'-dimethyl-2-aminoethyl) benzofur-5-yl]-4-chlorobenzamide

Beginning with 10 mg (0.046 mMol) 5-amino-2-methyl-3-(N',N'-dimethyl-2-aminoethyl)benzofuran and 12.1 mg (0.069 mMol) 4-chlorobenzoyl chloride, 10.6 mg (43%) of the title compound were prepared.

MS(m/e): 357(M⁺)

EXAMPLE 8

N-[2-methyl-3-(N',N'-dimethyl-2-aminoethyl) benzofur-5-yl]-2,4-difluorobenzamide Beginning with 10 mg (0.046 mMol) 5-amino-2-methyl-3-(N',N'-dimethyl-2-aminoethyl)benzofuran and 12.2 mg (0.069 mMol) 2,4-difluorobenzoyl chloride, 10.6 mg (43%) of the title compound were prepared.

MS(m/e): 358(M⁺)

EXAMPLE 9

N-[2-methyl-3-(N',N'-dimethyl-2-aminoethyl) benzofur-5-yl]-2-furamide

Beginning with 10 mg (0.046 mMol) 5-amino-2-methyl-3-(N',N'-dimethyl-2-aminoethyl)benzofuran and 9.0 mg (0.069 mMol) 2-furoyl chloride, 10.5 mg (49%) of the title compound were prepared.

MS (m/e): 313(M⁺)

EXAMPLE 10

N-[2-methyl-3-(N',N'-dimethyl-2-aminoethyl) benzofur-5-yl]thiophene-2-carboxamide Beginning with 10 mg (0.046 mMol) 5-amino-2-methyl-3-(N',N'-dimethyl-2-aminoethyl)benzofuran and 10.1 mg (0.069 mMol) 2-thiophenecarbonyl chloride, 10.2 mg (45%) of the title compound were prepared.

MS(m/e): 329(M⁺)

General procedure for the coupling of carboxylic acids with 5-aminobenzothiophenes and 5-aminobenzofurans To a suspension of 4 equivalents (1 mMol/gm) of polymer bound 1-ethyl-3-(3-(1-pyrrolidinylpropyl)carbodiimide (Preparation IX) in chloroform are added 1 equivalent of the appropriate 5-aminobenzothiophene or 5-aminobenzofuran and 1.5 equivalents of the desired carboxylic acid. The reaction is agitated for 48 hours at about 60° C. The resin is removed by filtration and the product isolated by evaporation of solvent. This procedure is illustrated by Examples 11–12.

EXAMPLE 11

N-[2-methyl-3-(N',N'-dimethyl-2-aminoethyl) benzofur-5-yl]methoxyacetamide

Beginning with 10 mg (0.046 mMol) 5-amino-2-methyl-3-(N',N'-dimethyl-2-aminoethyl)benzofuran and 6.2 mg (0.069 mMol) methoxyacetic acid, 7.0 mg (35%) of the title compound were prepared.

MS(m/e): 290(M⁺)

EXAMPLE 12

N-[2-methyl-3-(N',N'-dimethyl-2-aminoethyl) benzofur-5-yl]pyridine-4-carboxamide Beginning with 10 mg (0.046 mMol) 5-amino-2-methyl-3-(N',N'-dimethyl-2-aminoethyl)benzofuran and 8.5 mg (0.069 mMol) isonicotinic acid, 5.8 mg (26%) of the title compound were prepared.

MS(m/e): 323(M⁺)

EXAMPLE 13

N-[2-methyl-3-(N'-methyl-N'-[(fur-2-yl)methyl]-2-aminoethyl)benzofur-5-yl]-2-methyl-4-fluorobenzamide hydrochloride A mixture of 0.089 gm (0.27 mMol) N-[2-methyl-3-(N'-methyl-2-aminoethyl)benzofur-5-yl]-4-fluorobenzamide, 0.034 gm (0.35 mMol) 2-furaldehyde, 0.086 gm (0.41 mMol) sodium triacetoxyborohydride, and 0.059 gm (0.98 mMol) acetic acid in 10 mL dichloromethane was stirred at room temperature for 18 hours. Since the reaction was not complete by thin layer chromatography, an additional charge of 2-furaldehyde, sodium triacetoxyborohydride and acetic acid was made and stirring continued for an additional hour. The reaction mixture was partitioned between dichloromethane and 1N sodium hydroxide. The aqueous phase was separated and extracted again with dichloromethane. The organic phases were combined, dried over sodium sulfate and concentrated under reduced pressure. The residue was subjected to flash silica gel chromatography, eluting with ethyl acetate. Fractions containing product were combined and concentrated under reduced pressure to provide N-[2-methyl-3-(N'-methyl-N'-[(fur-2-yl)methyl]-2-aminoethyl)benzofur-5-yl]-2-methyl-4-fluorobenzamide as an oil. This oil was treated with hydrogen chloride to provide 0.083 gm (69%) of the title compound as a solid foam.

m.p.=67°–70° C.; MS(m/e): 406(M⁺)

EXAMPLE 14

N-[2-methyl-3-(N'-methyl-N'-[(thien-2-yl)methyl]-2-aminoethyl)benzofur-5-yl]-2-methyl-4-fluorobenzamide hydrochloride Beginning with 0.080 gm (0.25 mMol) N-[2-methyl-3-(N'-methyl-2-aminoethyl)benzofur-5-yl]-4-fluorobenzamide and 0.041 gm (0.35 mMol) thiophene-2-carboxaldehyde, 0.079 gm (70%) of the title compound were prepared by the procedure described in EXAMPLE 13.

MS(m/e): 422(M⁺)

EXAMPLE 15

N-[2-methyl-3-(N'-methyl-N'-[(thien-3-yl)methyl]-2-aminoethyl)benzofur-5-yl]-2-methyl-4-fluorobenzamide Beginning with 0.080 gm (0.25 mMol) N-[2-methyl-3-(N'-methyl-2-aminoethyl)benzofur-5-yl]-4-fluorobenzamide and 0.041 gm (0.35 mMol) thiophene-3-carboxaldehyde, 0.108 gm (100%) of the title compound were prepared by the procedure described in EXAMPLE 13.

MS(m/e): 422(M⁺)

EXAMPLE 16

N-[2-methyl-3-(N'-methyl-N'-[(5-methylfur-2-yl) methyl]-2-aminoethyl)benzofur-5-yl]-2-methyl-4-fluorobenzamide hydrochloride Beginning with 0.100 gm (0.31 mMol) N-[2-methyl-3-(N'-methyl-2-aminoethyl)benzofur-5-yl]-4- fluorobenzamide and 0.044 gm (0.40 mMol) 5-methyl-2-furaldehyde, 0.073 gm (52%) of the title compound were prepared by the procedure described in EXAMPLE 13.

m.p.=63°–68° C.; MS(m/e): 420(M⁺)

EXAMPLE 17

N-[2-methyl-3-(N'-methyl-N'-[(5-nitrofur-2-yl)methyl]-2-aminoethyl)benzofur-5-yl]-2-methyl-4-fluorobenzamide hydrochloride Beginning with 0.087 gm (0.27 mMol) N-[2-methyl-3-(N'-methyl-2-aminoethyl)benzofur-5-yl]-4-fluorobenzamide and 0.048 gm (0.34 mMol) 5-nitro-2-furaldehyde, 0.12 gm (92%) of the title compound were prepared by the procedure described in EXAMPLE 13.

m.p.=110°–115° C.; MS(m/e): 451(M⁺)

EXAMPLE 18

N-[3-(1-methylpiperidin-4-yl)benzofur-5-yl] methanesulfonamide hydrochloride

A mixture of 0.018 gm (0.07 mMol) 5-amino-3-(1-methylpiperidin-4-yl)benzofuran, 16.2 µL (0.21 mMol) methanesulfonyl chloride, and 0.100 gm (4 equivalents) of polymer bound piperidine in 1.5 mL dichloromethane. The reaction mixture was agitated for 24 hours at room temperature. The reaction mixture was then loaded onto a VARIAN BOND ELUT SCX™ (Varian, Harbor City, Calif., U.S.A.) ion exchange column, eluting first with several volumes of methanol and then with 10 mL 2M ammonia in methanol. Fractions containing product were combined and concentrated under reduced pressure. The residue was dissolved in methanolic hydrogen chloride and then the solvent removed. This step was repeated three times to provide 0.0061 gm of the title compound.

MS(m/e): 308(M⁺)

EXAMPLE 19

N-[3-(1-methylpiperidin-4-yl)benzofur-5-yl] acetamide hydrochloride

Beginning with a mixture of 0.018 gm (0.07 mMol) 5-amino-3-(1-methylpiperidin-4-yl)benzofuran and 15 µL (0.21 mMol) acetyl chloride, 0.0147 gm of the title compound were prepared by the procedure of EXAMPLE 18.

MS(m/e): 308(M⁺)

EXAMPLE 20

N-[3-(1-methylpiperidin-4-yl)benzofur-5-yl] phenylsulfonamide hydrochloride

Beginning with a mixture of 0.018 gm (0.07 mMol) 5-amino-3-(1-methylpiperidin-4-yl)benzofuran and 27 µL (0.21 inMol) phenylsulfonyl chloride, 0.0056 gm of the title compound were prepared by the procedure of EXAMPLE 18.

MS(m/e): 371(M+1)

EXAMPLE 21

N-[3-(1-methylpiperidin-4-yl)benzofur-5-yl]-O-methylcarbamate hydrochloride

Beginning with a mixture of 0.018 gm (0.07 mMol) 5-amino-3-(1-methylpiperidin-4-yl)benzofuran and 16.2 µL (0.21 mMol) methylchloroformate, 0.0128 gm of the title compound were prepared by the procedure of EXAMPLE 18.

MS(m/e): 289(M+1)

EXAMPLE 22

N-[3-(1-methylpiperidin-4-yl)benzofur-5-yl]-N'-phenylurea hydrochloride

Beginning with a mixture of 0.018 gm (0.07 mMol) 5-amino-3-(1-methylpiperidin-4-yl)benzofuran and 23 µL (0.21 mMol) phenylisocyanate, 0.0089 gm of the title compound were prepared by the procedure of EXAMPLE 18.

MS(m/e): 349(M⁺)

To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90, 408–412 (1993).

Membrane Preparation: Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [³H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 µL of buffer (50 mM Tris, 10 mM MgCl$_2$, 0.2 mM EDTA, 10 µM pargyline, 0.1% ascorbate, pH=7.4 at 37° C.) in 96 well microtiter plates. Saturation studies were conducted using [³H]5-HT at 12 different concentrations ranging from 0.5 nM to 100 nM. Displacement studies were performed using 4.5–5.5 nM [³H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 µM 5-HT. Binding was initiated by the addition of 50 µL membrane homogenates (10–20 µg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [³H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. Representative compounds of the present invention were found to have an affinity at the 5-$HT_{1F}$ receptor of $K_i<1.5$ mM.

As was reported by R. L. Weinshank, et al., WO93/14201, the 5-$HT_{1F}$ receptor is functionally coupled to a G-protein as measured by the ability of serotonin and serotonergic drugs to inhibit forskolin stimulated cAMP production in NIH3T3 cells transfected with the 5-$HT_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra.; R. L. Weinshank, et al., *Proceedings of the National Academy of Sciences (USA)*, 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% $CO_2$. Drug dose-effect curves were then conducted by adding 6 different final concentrations of drug, followed immediately by the addition of forskolin (10 µM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 µM). The plates were stored at 4° C. for 15 minutes and then centrifuged for 5 minutes at 500×g to pellet cellular debris, and the supernatant was aliquoted and stored at –20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software.

The discovery that the pain associated with migraine and associated disorders is inhibited by agonists of the 5-$HT_{1F}$ receptor required the analysis of data from diverse assays of pharmacological activity. To establish that the 5-$HT_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-$HT_{1F}$ receptor subtype was performed as described supra. For comparison purposes, the binding affinities of compounds to the 5-$HT_{1D\alpha}$, 5-$HT_{1D\beta}$, 5-$HT_{1E}$ and 5-$HT_{1F}$ receptors were also determined as described supra, except that different cloned receptors were employed in place of the 5-$HT_{1F}$ receptor clone employed therein. The same panel was then tested in the cAMP assay to determine their agonist or antagonist character at each of the 5-$HT_{1D\alpha}$, 5-$HT_{1D\beta}$, 5-$HT_{1E}$ and 5-$HT_{1F}$ receptor subtypes. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

COMPOUND I

3-[2-(dimethylamino)ethyl]-N-methyl-1H-indole-5-methanesulfonamide butane-1,4-dioate (1:1)

(Sumatriptan succinate)

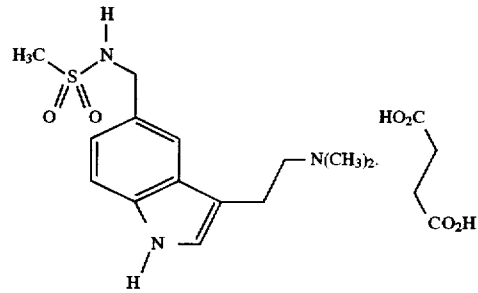

Sumatriptan succinate is commercially available as Imitrex™ or may be prepared as described in U.S. Pat. No. 5,037,845, issued Aug. 6, 1991, which is herein incorporated by reference.

COMPOUND II 5-fluoro-3-<1-<2-<1-methyl-1H-pyrazol-4-yl>ethyl>-4-piperidinyl>-1H-indole hydrochloride

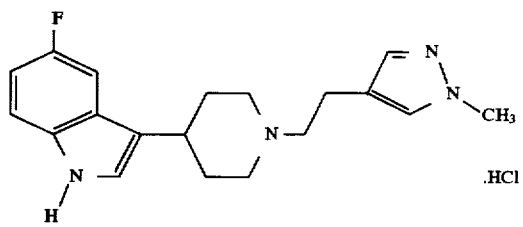

COMPOUND III 5-hydroxy-3-(4-piperidinyl)-1H-indole oxalate

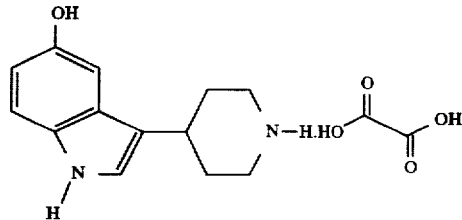

COMPOUND IV 8-chloro-2-diethylamino-1,2,3,4-tetrahydronaphthalene hydrochloride

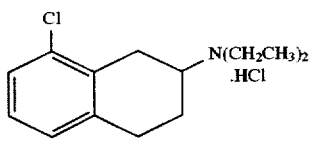

COMPOUND V 6-hydroxy-3-dimethylamino-1,2,3,4-tetrahydrocarbazole

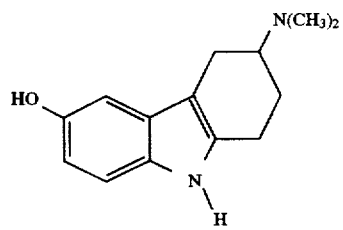

Compounds II, III, IV and V are described in U.S. Pat. No. 5,521,196, issued May 28, 1996, which is herein incorporated by reference in its entirety.

Binding Assays

The binding affinities of compounds for various serotonin receptors were determined essentially as described above except that different cloned receptors are employed in place of the 5-$HT_{1F}$ receptor clone employed therein. The results of these binding experiments are summarized in Table II.

TABLE II

BINDING TO SEROTONIN (5-$HT_1$) RECEPTOR SUBTYPES ($K_i$ nM)

| Compound | 5-$HT_{1D\alpha}$ | 5-$HT_{1D\beta}$ | 5-$HT_{1E}$ | 5-$HT_{1F}$ |
|---|---|---|---|---|
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

All of the compounds of the panel were tested in the cAMP formation assay described supra and all were found to be agonists of the 5-$HT_{1F}$ receptor.

Protein Extravasation

Harlan Sprague-Dawley rats (250–350 g) or guinea pigs from Charles River Laboratories (250–350 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 MA (5 Hz, 4 msec duration) with a Model 273 potentiostat/ galvanostat (EG&G Princeton Applied Research).

Fifteen minutes following stimulation, the animals were killed by exsanguination with 40 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 μm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. This data is presented in Table III.

TABLE III

Inhibition of Protein Extravasation ($ID_{50}$ mMol/kg)

| Compound | i.v. $ID_{50}$ (mMol/kg) |
|---|---|
| I | $2.6 \times 10^8$ |
| II | $8.6 \times 10^{10}$ |
| III | $8.9 \times 10^9$ |
| IV | $1.2 \times 10^7$ |
| V | $8.7 \times 10^9$ |

To determine the relationship of binding at various serotonin receptors to inhibition of neuronal protein extravasation, the binding affinity of all of the compounds to each of the 5-$HT_{1D\alpha}$, 5-$HT_{1D\beta}$, 5-$HT_{1E}$ and 5-$HT_{1F}$ receptors was plotted against their $ID_{50}$ in the protein extravasation model. A linear regression analysis was performed on each set of data and a correlation factor, $R^2$, calculated. The results of this analysis are summarized in Table IV.

TABLE IV

Correlation Factor ($R^2$) for Specific 5-HT$_1$ Subtype Binding Affinity vs Inhibition of Protein Extravasation

| 5-HT$_1$ Subtype | Correlation Factor ($R^2$) |
|---|---|
| 5-HT$_{1D\alpha}$ | 0.07 |
| 5-HT$_{1D\beta}$ | 0.001 |
| 5-HT$_{1E}$ | 0.31 |
| 5-HT$_{1F}$ | 0.94 |

An ideally linear relationship would generate a correlation factor of 1.0, suggests a cause and effect relationship between the two variables. The experimentally determined correlation factor between inhibition of neuronal protein extravasation and 5-HT$_{1F}$ binding affinity is 0.94. This nearly ideal dependence of the ID$_{50}$ in the protein extravasation model on binding affinity to the 5-HT$_{1F}$ receptor clearly demonstrates that the 5-HT$_{1F}$ receptor mediates the inhibition of protein extravasation resulting from stimulation of the trigeminal ganglia.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 1 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 12 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A compound of the formula

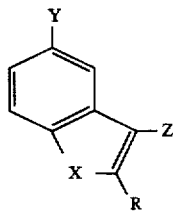

I in which

X is O or S;

Y is $R^4C(O)NH—$, $R^5R^6NC(Q)NH—$, $R^7OC(O)NH—$, or $R^8SO_2NH—$;

Z is a structure of formula:

(a)

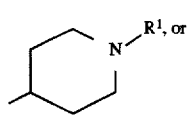

(b)

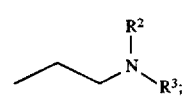

R is hydrogen or $C_1–C_4$ alkyl;

$R^1$ is hydrogen or $C_1–C_4$ alkyl;

$R^2$ is $C_1–C_4$ alkyl, $C_3–C_8$ cycloalkyl, cycloalkyl-($C_1–C_3$ alkylene), aryl-($C_1–C_3$ alkylene), or heteroaryl-($C_1–C_3$ alkylene);

$R^3$ is hydrogen or $C_1–C_4$ alkyl;

$R^4$ is $C_1–C_4$ alkyl, $C_1–C_4$ alkoxy substituted $C_1–C_4$ alkyl, $C_3–C_7$ cycloalkyl, phenyl, substituted phenyl, biphenylyl, naphthyl, or a heterocycle;

$R^5$ and $R^6$ are independently selected from the group consisting of hydrogen, $C_1–C_6$ alkyl, $C_3–C_6$ alkenyl, $C_3–C_8$ cycloalkyl, phenyl, substituted phenyl, phenyl ($C_1–C_4$ alkylene), phenyl($C_1–C_4$ alkylene) substituted in the phenyl ring, (($C_1–C_4$ alkyl or $C_1–C_4$ alkoxycarbonyl substituted)$C_1–C_4$ alkyl)phenyl, and $C_1–C_4$ alkyl α-substituted with $C_1–C_4$ alkoxycarbonyl; or $R^5$ and $R^6$ taken together with the nitrogen atom to which they are attached form a pyrrolidine, piperidine, piperazine, 4-substituted piperazine, morpholine or thiomorpholine ring;

$R^7$ is $C_1–C_6$ alkyl, $C_3–C_6$ alkenyl, phenyl, substituted phenyl, $C_3–C_8$ cycloalkyl, or $C_1–C_4$ alkyl ω-substituted with $C_1–C_4$ alkoxy;

$R^8$ is $C_1–C_4$ alkyl, phenyl, substituted phenyl, or di($C_1–C_4$ alkyl)amino;

Q is S or O, and pharmaceutically acceptable acid addition salts thereof.

2. A compound of claim 1 where Z is a structure of formula (a).

3. A compound of claim 2 where $R^1$ is methyl.

4. A compound of claim 1 where Z is a structure of formula (b).

5. A compound of claim 4 where $R^2$ is heteroaryl-($C_1–C_3$ alkylene).

6. A compound of claim 4 where $R^3$ is methyl.

7. A compound of claim 1 where X is O.

8. A compound of claim 7 where Y is $R^4C(O)NH—$.

9. A compound of claim 8 where $R^4$ is a heterocycle.

10. A compound of claim 8 where $R^4$ is phenyl or substituted phenyl.

11. A method for the treatment or prevention of migraine comprising administering to a mammal suffering from or susceptible to migraine an effective amount of a compound of claim 1.

12. The method of claim 11 where the mammal is a human.

13. A pharmaceutical formulation which comprises, in association with a pharmaceutically acceptable carrier, diluent or excipient, a compound of claim 1.

14. A method for activation of $5\text{-}HT_{1F}$ receptors in mammals comprising administering to a mammal in need of such activation a pharmaceutically effective amount of a compound of formula:

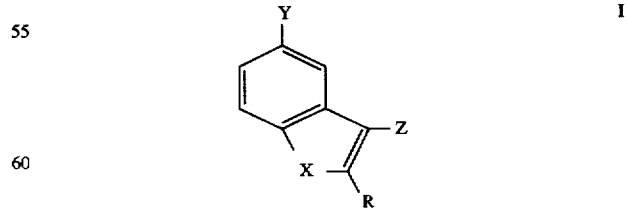

I in which

X is O or S;

Y is $R^4C(O)NH—$, $R^5R^6NC(Q)NH—$, $R^7OC(O)NH—$, or $R^8SO_2NH—$;

Z is a structure of formula:

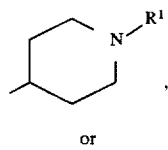 (a)

or

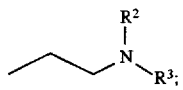 (b)

R is hydrogen or $C_1$–$C_4$ alkyl;

$R^1$ is hydrogen or $C_1$–$C_4$ alkyl;

$R^2$ is $C_1$–$C_4$ alkyl, $C_3$–$C_8$ cycloalkyl, cycloalkyl-($C_1$–$C_3$ alkylene), aryl-($C_1$–$C_3$ alkylene), or heteroaryl-($C_1$–$C_3$ alkylene);

$R^3$ is hydrogen or $C_1$–$C_4$ alkyl;

$R^4$ is $C_1$–$C_4$ alkyl, $C_1$–$C_4$ alkoxy substituted $C_1$–$C_4$ alkyl, $C_3$–$C_7$ cycloalkyl, phenyl, substituted phenyl, biphenylyl, naphthyl, or a heterocycle;

$R^5$ and $R^6$ are independently selected from the group consisting of hydrogen, $C_1$–$C_6$ alkyl, $C_3$–$C_6$ alkenyl, $C_3$–$C_8$ cycloalkyl, phenyl, substituted phenyl, phenyl ($C_1$–$C_4$ alkylene), phenyl($C_1$–$C_4$ alkylene) substituted in the phenyl ring, (($C_1$–$C_4$ alkyl or $C_1$–$C_4$ alkoxycarbonyl substituted)$C_1$–$C_4$ alkyl)phenyl, and $C_1$–$C_4$ alkyl α-substituted with $C_1$–$C_4$ alkoxycarbonyl; or $R^5$ and $R^6$ taken together with the nitrogen atom to which they are attached form a pyrrolidine, piperidine, piperazine, 4-substituted piperazine, morpholine or thiomorpholine ring;

$R^7$ is $C_1$–$C_6$ alkyl, $C_3$–$C_6$ alkenyl, phenyl, substituted phenyl, $C_3$–$C_8$ cycloalkyl, $C_1$–$C_4$ alkyl ω-substituted with $C_1$–$C_4$ alkoxy;

$R^8$ is $C_1$–$C_4$ alkyl, phenyl, substituted phenyl, or di($C_1$–$C_4$ alkyl)amino;

Q is S or O, and pharmaceutically acceptable acid addition salts thereof.

* * * * *